United States Patent
Amroabadi et al.

(10) Patent No.: US 9,373,159 B2
(45) Date of Patent: Jun. 21, 2016

(54) METHOD AND SYSTEM FOR COMPRESSED SENSING IMAGE RECONSTRUCTION

(71) Applicant: University Health Network, Toronto (CA)

(72) Inventors: Sayed Masoud Hashemi Amroabadi, Toronto (CA); Patrick R. Gill, Toronto (CA); Narinder S. Paul, Richmond Hill (CA)

(73) Assignee: UNIVERSITY HEALTH NETWORK, Toronto, Ontario (CA)

( * ) Notice: Subject to any disclaimer, the term of this patent is extended or adjusted under 35 U.S.C. 154(b) by 0 days.

(21) Appl. No.: 14/409,212

(22) PCT Filed: Jun. 18, 2013

(86) PCT No.: PCT/CA2013/000582
§ 371 (c)(1),
(2) Date: Dec. 18, 2014

(87) PCT Pub. No.: WO2013/188957
PCT Pub. Date: Dec. 27, 2013

(65) Prior Publication Data
US 2015/0187052 A1      Jul. 2, 2015

Related U.S. Application Data

(60) Provisional application No. 61/660,948, filed on Jun. 18, 2012.

(51) Int. Cl.
*G06K 9/00*      (2006.01)
*A61B 6/00*      (2006.01)
(Continued)

(52) U.S. Cl.
CPC ............... *G06T 5/001* (2013.01); *A61B 6/5205* (2013.01); *G01R 33/5611* (2013.01);
(Continued)

(58) Field of Classification Search
CPC ............... A61B 5/00; A61B 6/00; G06K 9/00
USPC .............. 382/128–134; 378/4, 8, 21–27, 101, 378/901
See application file for complete search history.

(56) References Cited

U.S. PATENT DOCUMENTS 7,616,795 B2 * 11/2009 Lutz ....................... A61B 6/032
382/128
7,778,455 B2 * 8/2010 Araikum ................. G06T 5/003
382/131

(Continued)

OTHER PUBLICATIONS

David J. Brenner, Carl D. Elliston, Eric J. Hall and Walter E. Berdon, "Estimated risks of radiation-induced fatal cancer from pediatric CT", American Journal of Roentgenology, 2001, 176: 289-96.

(Continued)

*Primary Examiner* — Abolfazl Tabatabai
(74) *Attorney, Agent, or Firm* — Norton Rose Fulbright Canada LLP; Maya Medeiros

(57) ABSTRACT

A Compressed Sensing (CS) based image reconstruction method and system is described herein which may be used to reduce the X-ray dose radiation in Computed Tomography (CT) or to decrease the scan duration in MR imaging (MRI). Methods and systems described herein may address problems that have hindered the clinical usage of CS, i.e. computation complexity and modeling problems. Using the described algorithm, high quality images may be recovered from undersampled data which may help to reduce the scan time and the exposed invasive radiations. Using the same set of data in conventional image reconstruction algorithms (e.g. Filtered Back Projection (FBP) in CT) may cause severe streak artifacts and may take significantly more time using Graphics Processing Units (GPU) and parallel clusters with the conventional CS-based methods. This method can be used other imaging modalities using Radon transform (such as C-Arm and electron tomography, for example).

18 Claims, 16 Drawing Sheets

(51) Int. Cl.
*G06T 5/00* (2006.01)
*G01R 33/561* (2006.01)
*G06T 11/00* (2006.01)
*G06T 7/00* (2006.01)
*A61B 6/03* (2006.01)
*A61B 5/055* (2006.01)

(52) U.S. Cl.
CPC ............ *G06T 7/0012* (2013.01); *G06T 11/006* (2013.01); *A61B 5/055* (2013.01); *A61B 6/03* (2013.01); *A61B 6/501* (2013.01); *G06T 2211/424* (2013.01); *G06T 2211/436* (2013.01)

(56) References Cited

U.S. PATENT DOCUMENTS

| | | | | |
|---|---|---|---|---|
| 8,948,337 | B2* | 2/2015 | Pack | G06T 11/006 378/4 |
| 2008/0221425 | A1* | 9/2008 | Olson | A61B 19/52 600/407 |
| 2010/0121183 | A1* | 5/2010 | Taguchi | A61B 6/5264 600/427 |
| 2010/0226474 | A1* | 9/2010 | Yamakawa | A61B 6/032 378/5 |
| 2010/0246920 | A1* | 9/2010 | Vaswani | G06K 9/00523 382/131 |
| 2011/0052035 | A1* | 3/2011 | Kirchberg | A61B 6/481 382/132 |

OTHER PUBLICATIONS

John A. Ambrose and Valentin Fuster, "The risk of coronary occlusion is not proportional to the prior severity of coronary stenoses", Heart, 1998; 79: 3-4.

Thomas J. Ryan, "The coronary angiogram and its seminal contributions to cardiovascular medicine over five decades", Circulation, 2002; 106: 752-756.

C. Di Mario, G. Gorge, R. Peters, et al.,"Clinical application and image interpretation in intracoronary ultrasound", European Heart Journal, 1998; 19: 207-229.

Harpreet K. Pannu, Thomas G. Flohr, Frank M. Corl and Elliott K. Fishman, "Current Concepts in Multi-Detector Row CT Evaluation of the Coronary Arteries: Principles, Techniques, and Anatomy", RadioGraphics, 2003; 23: S111-S125.

Emmanuel J. Candes, Justin Romberg and Terence Tao, "Robust uncertainty principles: Exact signal reconstruction from highly incomplete frequency information", IEEE Transactions on Information Theory, 2006; 52(2): 489-509.

Jose M. Bioucas-Dias and Mario A.T. Figueiredo, "A New TwIST: Two-Step Iterative Shrinkage/Thresholding Algorithms for Image Restoration", IEEE Transactions on Image Processing, 2007; 16(12): 2992-3004.

Henry Stark, John W. Woods, Indraneel Paul and Rajesh Hingorani, "Direct Fourier Reconstruction in Computer Tomography", IEEE Transactions on Acoustics, Speech, and Signal Processing, 1981; 29(2): 237-245.

David Gottlieb, Bertil Gustafsson and Patrick Forssen, "On the Direct Fourier Method for Computer Tomography", IEEE Transactions on Medical Imaging, 2000; 19(3): 223-232.

Guy M. Besson, "CT image reconstruction from fan-parallel projection data," Nuclear Science Symposium, 1998. Conference Record. 1998 IEEE (Volume:3 ), 1644-1648.

Junfeng Yang, Yin Zhang and Wotao Yin, "A Fast Alternating Direction Method for TVL1-L2 signal reconstruction from Partial Fourier Data", IEEE Journal of Selected Topics in Signal Processing Special Issue on Compressed Sensing, 2010; 4(2): 288-297.

H. Bruder, R. Raupach, J. Sunnegardh, M. Sedlmair, K. Stierstorfer and T. Flohr, "Adaptive iterative reconstruction", Proc. of SPIE, 2011; 7691: 76910J-1-76910J-12.

Hui Peng and Henry Stark, "Direct Fourier Reconstruction in Fan-Beam Tomography", IEEE Transactions on Medical Imaging, 1987; MI-6(3): 209-219.

* cited by examiner 402 404

418

416

420

422

424

426

432

434

430

428

444

446

442

440

452

454

450

448

462

460

METHOD AND SYSTEM FOR COMPRESSED SENSING IMAGE RECONSTRUCTION

FIELD OF THE INVENTION

The present disclosure relates to methods and systems for compressed sensing image reconstruction. In particular, the present disclosure relates to methods and systems suitable for use in medical imaging reconstruction, such as in computed tomography (CT), magnetic resonance imaging (MRI), c-arm scanning, electron tomography, and other imaging modalities.

INTRODUCTION

CT utilization has increased dramatically over the last two decades; principally due to the unsurpassed speed and detail with which cross sectional views of soft tissue and organs can be obtained. However, CT scans may deliver a relatively large radiation dose to patients, giving rise to concerns that this may result in an increased risk of developing cancer. Using a known image reconstruction algorithm, Filtered Back Projection (FBP), low dose CT images suffer from low contrast to noise ratio which decreases the detectability of the lesions. As a result, a low dose CT scan technique that generates a high quality reconstructed image is desirable. As an illustrative and non-limiting example, cardiac CT scans may provide excellent images of the heart, yet with current techniques they may be used sparingly to minimize the patient's radiation dose. By some estimates, in certain populations the radiation caused by CT imaging may be responsible for up to 2% of all cancer deaths. See for example, D. J. Brenner, C. D. Elliston, E. J. Hall and W. E. Berdon, Estimated risks of radiation-induced fatal cancer from pediatric CT, American Journal of Roentgenology, 2001, 176 (2): 289-96, the entire contents of which is hereby incorporated by reference. Cardiac CT scans have been found to give some of the highest doses of any type of CT scan because they typically image low-density tissue; higher doses allow for lower-noise images. Moreover, since the heart typically must be at rest while a cardiac CT scan is in progress, often only incomplete scan data may be safely available, especially in patients with an elevated heart rate.

A signal processing technique referred to as compressed sensing may theoretically enable full image reconstruction based on noisy, partial scan data. Compressed sensing typically uses math to derive an image that conforms both to the observed data and to expectations of what the image should look like. In general, these assumptions may be non-specific; for example the assumption that the image be wavelet-compressible, or that the majority of pairs of adjacent pixels have similar values may be both suitable for the purposes of compressed sensing.

Compressed sensing and its application to CT scanning has been demonstrated before in a variety of ways: iterative reconstruction methods have been found to reduce the noise effects in the low dose images somewhat, while compressed sensing may be prohibitively slow using current techniques. See for example, G. H. Chen, J. Tang, and S. Leng, "Prior image constrained compressed sensing (piccs): A method to accurately reconstruct dynamic ct images from highly undersampled projection data sets," Medical Physics, vol. 35, no. 2, pp. 660-663, February 2008, the entire contents of which is hereby incorporated by reference. See for another example, U.S. Publication No. 2009/0196393.

Cardiovascular disease may be currently one of the leading causes of mortality in Canadian patients, representing 30% of all male deaths and 31% of all female deaths, with coronary artery disease (CAD) responsible for over half of these deaths. The pathogenesis of CAD typically involves the formation of intimal arterial plaque due to complex interactions leading to endothelial injury, vascular inflammation and a fibroproliferative response. See for example, W. Grossman and D. S. Baim, Grossman's Cardiac Catheterization, Angiography and Intervention, 6th edition Philadelphia, LippincottWilliams & Wilkins, 2000, the entire contents of which is hereby incorporated by reference. This process may cause a gradual reduction in the arterial lumen until a hemodynamically significant stenosis occurs, usually when the luminal diameter has narrowed by more than 70% (see for example, J. A. Ambrose, and V. Fuster, "The risk of coronary occlusion is not proportional to the prior severity of coronary stenoses," Heart, 1998; 79: 3-4, the entire contents of which is hereby incorporated by reference) and the patient may develop symptomatic ischemic heart disease. Catheter coronary angiography (CCA) is the current "Gold Standard" for direct visualization of coronary artery patency, but it is typically an invasive and expensive procedure with associated morbidity and mortality (see for example, D. C. Levin, "Invasive evaluation (coronary arteriography) of the coronary artery disease patient: clinical, economic, and social issues," Circulation, 1982; 66:71-9, T. J. Ryan, "The coronary angiogram and its seminal contributions to cardiovascular medicine over five decades," Circulation, 2002; 106:752-6, the entire contents of each is hereby incorporated by reference) and the technique is typically limited to estimation of lumen patency. However, there are patients who may experience an acute cardiac event, such as sudden cardiac death, with lesions that hitherto had been hemodynamically insignificant. These patients are thought to have vulnerable plaque: a lesion that is intrinsically prone to rupture due to a predominant fatty composition and a thin fibrous cap (see for example P. R. Moreno, "Vulnerable Plaque: Definition, Diagnosis, and Treatment," Cardiology Clinics, 2010; 28: 1-30). These lesions are thought to be susceptible to sheer stress, subsequent rupture and haemorrhage with conversion of a non-obstructive plaque into one causing significant luminal stenosis. The current imaging gold standard for determining in vivo plaque composition is intra-vascular ultrasound (IVUS). However, this is also typically an invasive, time intensive and expensive technique with limited patient access. See for example, C. Di Mario, G. Grge, R. Peters, et al. "Clinical application and image interpretation in intracoronary ultrasound," Eur Heart J, 1998; 19: 207-229, the entire contents of which is hereby incorporated by reference.

The need for non-invasive diagnostic alternatives for coronary artery imaging may have facilitated the clinical introduction of CT coronary angiography (CTCA) for excluding hemodynamically significant coronary artery disease (CAD) and in the detection of vulnerable plaque. CTCA has been found to have a negative predictive value in excess of 98% in the ideal patient for excluding hemodynamically significant coronary artery disease. See for example, K. H. Pannu, T. G. Flohr, F. M. Corl, and E. K. Fishman, "Current Concepts in Multi-Detector Row CT Evaluation of the Coronary Arteries: Principles, Techniques, and Anatomy," Radiographics, 2003; 23: S111-S125. However, there may be one or more limitations in the use of current CT technology for accurate evaluation of coronary patency and plaque characterization, including in-plane temporal resolution, spatial resolution, contrast resolution, and radiation dose which may be addressed by embodiments described herein.

Compressed sensing has been used in U.S. Publication No. 2010/0207629 (CT, MRI, C-Arm) and U.S. Publication No. 2009/0196393 in which the forward and backward matrix multiplication is used which makes it computationally intensive. Partial Fourier transform is used in U.S. Publication No. 2011/0058719 (for MRI specifically) combined with CS. However, most available CS-based reconstruction techniques are either prohibitively computationally intensive using large discretized Radon transform matrix or make unphysical assumptions to avoid the polar to Cartesian domain conversion and accelerate the algorithm, which may be addressed by embodiments described herein.

SUMMARY

In a first aspect, embodiments described herein may provide a method for image reconstruction, the method may include: receiving signals representing a set of raw image data in the projection domain or raw data domain; performing a 1-dimensional Fourier transform on the set of raw image data to convert the set of raw image data into the partial Fourier domain; determining a set of reconstructed or recovered image data from the set of raw image data in the partial Fourier domain, based on an optimization model; performing an inverse operation on the set of reconstructed or recovered image data to convert the set of reconstructed or recovered image data into the image domain; and generating signals representing the set of reconstructed or recovered image data.

In some example embodiments, the optimization model may be based on a set of basis data in the Wavelet, Curvelet or any other sparsifying transform domain.

In some example embodiments, the optimization model may be further based on a set of selected regularization parameters.

In some example embodiments, the method may include determining an interpolation of the set of raw image data in the Fourier domain from a polar coordinate system to a pseudo-polar or Cartesian coordinate system.

In some example embodiments, the method may include applying a weighting to each data point in the pseudo-polar or Cartesian coordinate system, based on a known amount of confidence in interpolation between the polar coordinate system and the Cartesian or pseudo-polar coordinate system.

In some example embodiments, the set of raw image data in the projection domain or raw data domain may be based on non-parallel beam geometries, and the method may include rebinning the set of raw image data in the projection domain or raw data domain based on parallel beam geometries.

In some example embodiments, the set of raw image data in the projection domain or raw data domain may be acquired using computed tomography (CT) imaging, parallel beam CT scanning, cone beam CT scanning, C-arm scanning, helical CT, scanning MRI or other imaging modality.

In some example embodiments, the set of raw image data in the projection domain or raw data domain may be a set of incomplete raw image data, a set of complete raw image data or a set of overcomplete raw image data.

In some example aspects, the present disclosure provides a system for image reconstruction, the system comprising a processor coupled to a memory having computer-readable instructions recorded thereon, the computer-readable instructions, when executed, may cause the system to carry out one or more of the methods described herein.

In some examples, the system may include a display coupled to the processor for displaying the set of reconstructed or recovered image data as a reconstructed or recovered image.

In some examples, the system may include an imaging workstation.

DRAWINGS

Various embodiments will now be described, by way of example only, with reference to the following drawings, in which.

Figure 12:
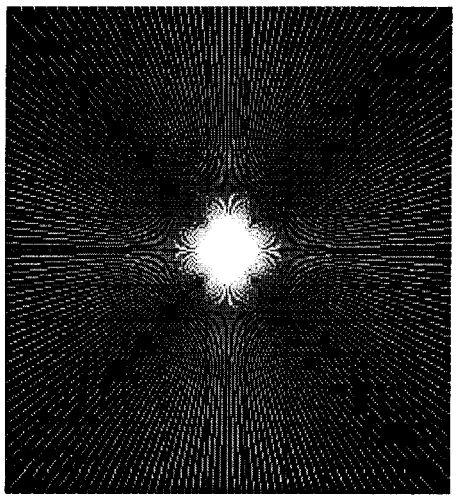
Figure 12:
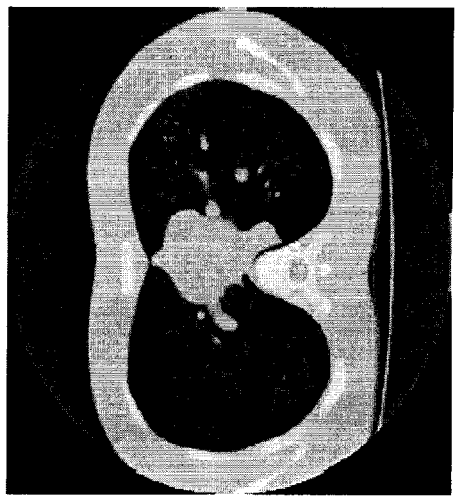
Figure 12:
Figure 12:
Figure 13:
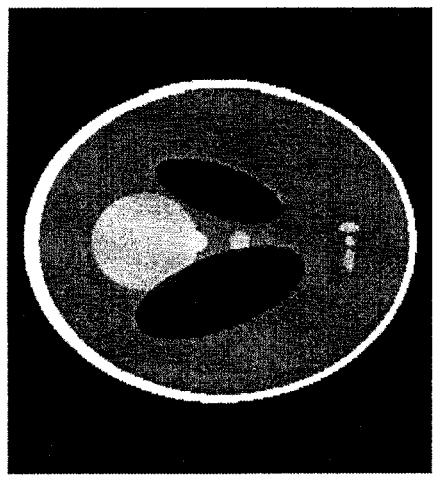
Figure 13:
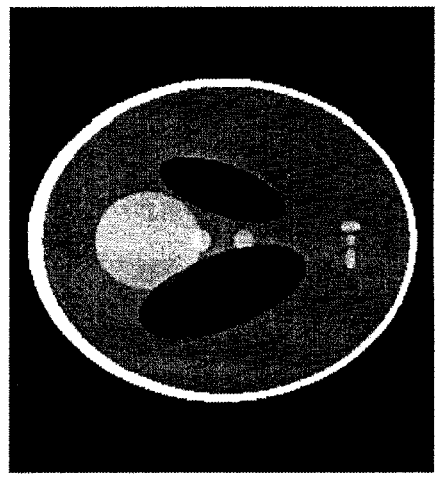
Figure 13:
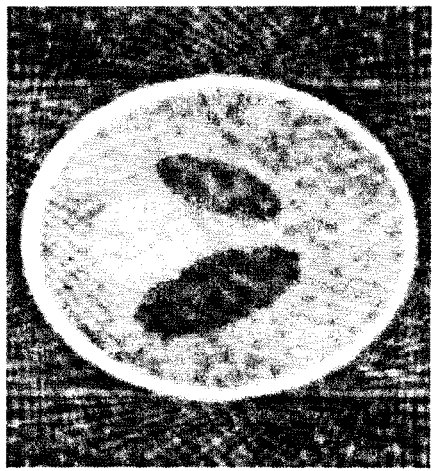
Figure 13:
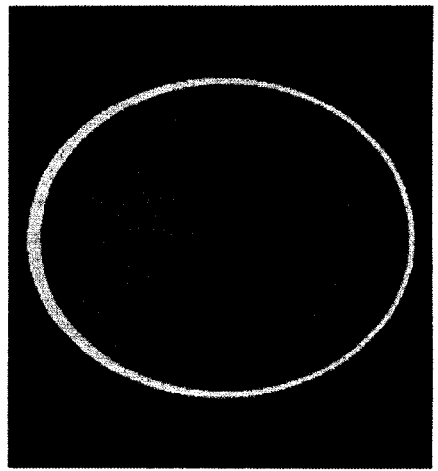
Figure 14:
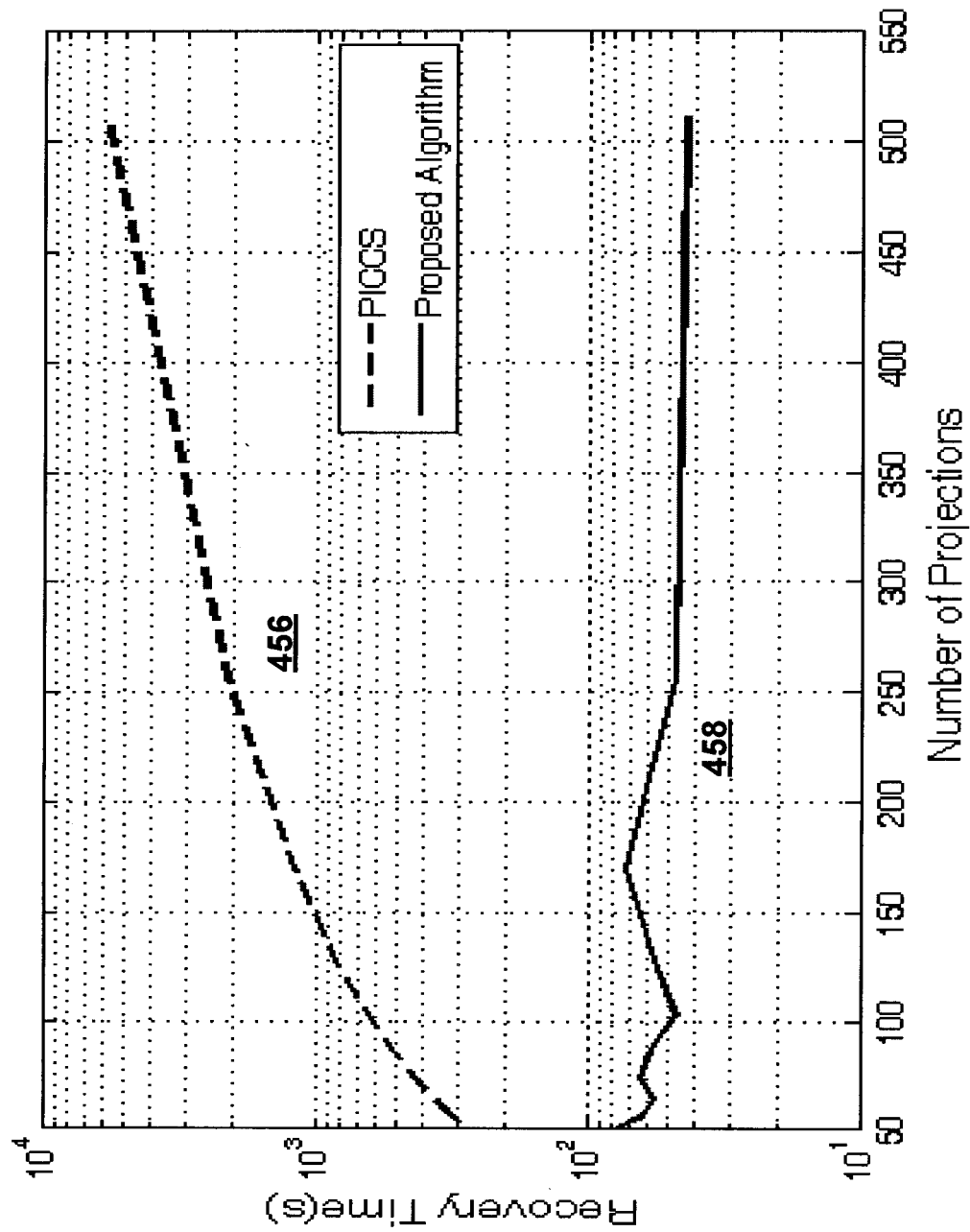
Figure 15:
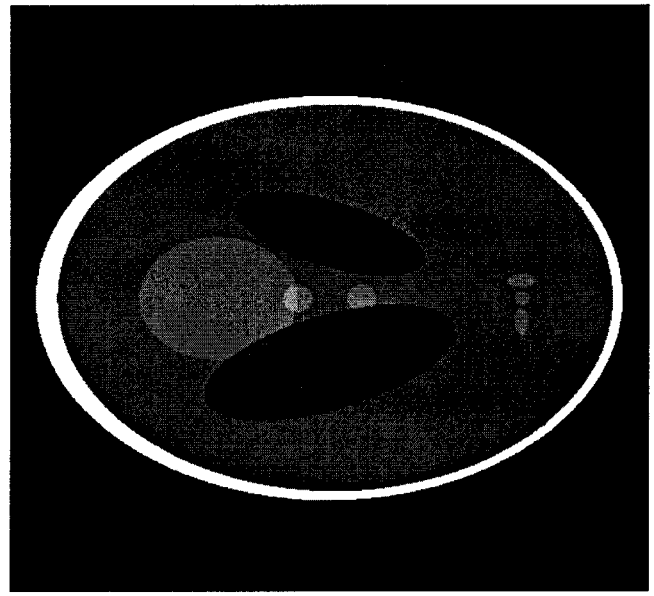
Figure 15:
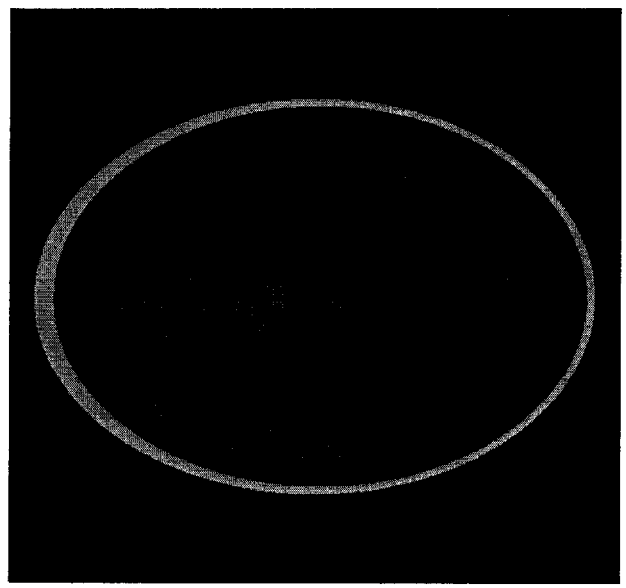
Figure 16:
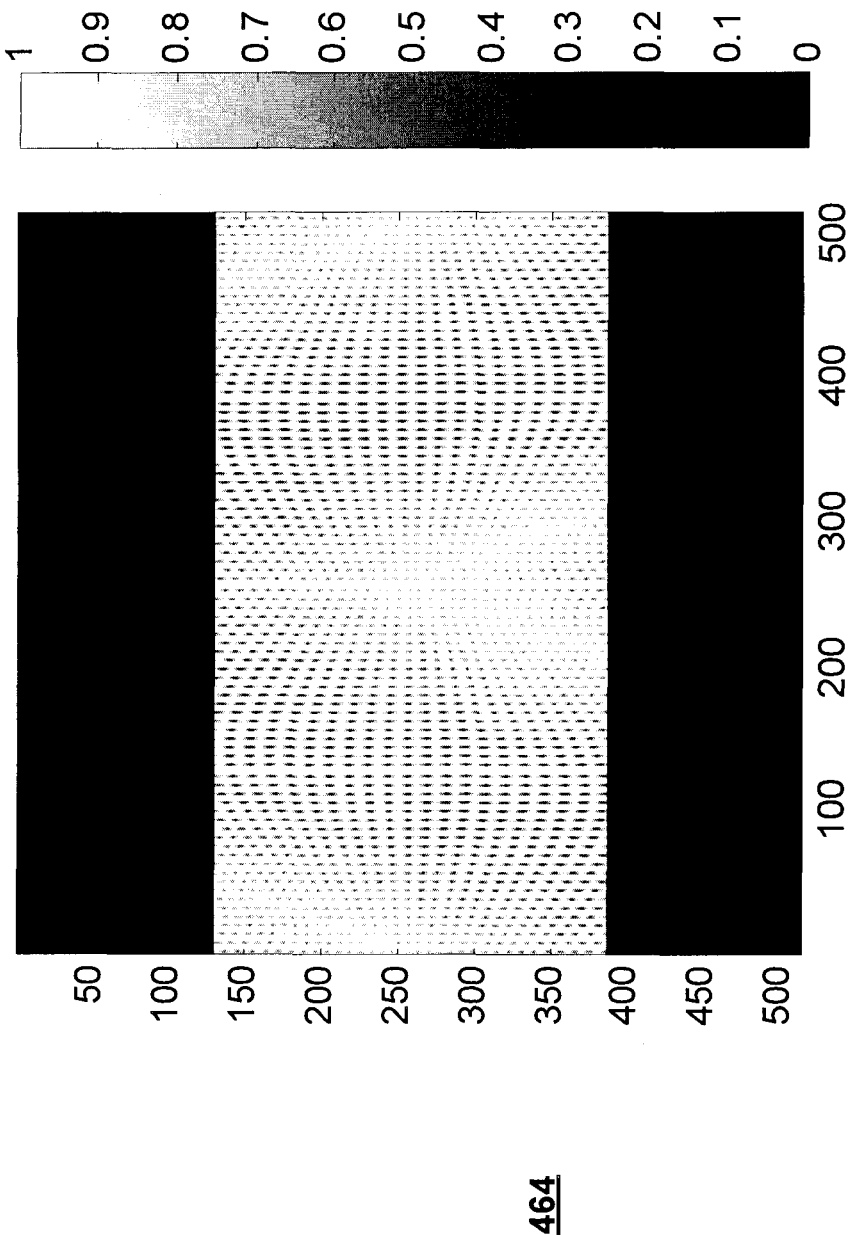

FIG. 12 a further illustrative example of comparison of images including an image generated using FBP and a reconstructed image generated according to compressed sensing image reconstruction according to some embodiments;

FIG. 13 is a further illustrative example of comparison of images based on different confidence coefficients;

FIG. 14 is an example chart comparing computation time for an Algebraic Reconstruction Technique (ART) Total variation minimization based method which use matrix multiplication (such as PICCS for example) and the compressed sensing image reconstruction according to some embodiments;

FIG. 15 is another illustrative example of comparison of images with different confidence matrices according to some embodiments; and FIG. 16 is an illustrative example of a confidence matrix.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments generally described herein.

DESCRIPTION OF VARIOUS EMBODIMENTS

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the various programmable computers may be a server, network appliance, set-top box, embedded device, computer expansion module, personal computer, laptop, personal data assistant, cellular telephone, smartphone device, UMPC tablets and wireless hypermedia device or any other computing device capable of being configured to carry out the methods described herein.

Program code is applied to input data to perform the functions described herein and to generate output information. The output information is applied to one or more output devices, in known fashion. In some embodiments, the communication interface may be a network communication interface. In embodiments in which elements of the invention are combined, the communication interface may be a software communication interface, such as those for inter-process communication (IPC). In still other embodiments, there may be a combination of communication interfaces implemented as hardware, software, and combination thereof.

Each program may be implemented in a high level procedural or object oriented programming or scripting language, or both, to communicate with a computer system. However, alternatively the programs may be implemented in assembly or machine language, if desired. The language may be a compiled or interpreted language. Each such computer program may be stored on a storage media or a device (e.g., ROM, magnetic disk, optical disc), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the systems and methods of the described embodiments are capable of being distributed in a computer program product including a physical, non-transitory computer readable medium that bears computer usable instructions for one or more processors. The medium may be provided in various forms, including one or more diskettes, compact disks, tapes, chips, magnetic and electronic storage media, volatile memory, non-volatile memory and the like. Non-transitory computer-readable media may include all computer-readable media, with the exception being a transitory, propagating signal. The term non-transitory is not intended to exclude computer readable media such as primary memory, volatile memory, RAM and so on, where the data stored thereon may only be temporarily stored. The computer useable instructions may also be in various forms, including compiled and non-compiled code.

Embodiments described herein provide systems and methods for compressed sensing image reconstructions. The application of CS in medical imaging has been a research topic as an attempt to reduce the X-ray radiation in CT, to increase the image quality in some other modalities like electron tomography, to decrease the scan duration in MRI, and the like. However, excessive computation times may make it clinically unrealized.

Embodiments described herein may use a some or all of a combination of conebeam and fan beam to parallel beam rebinning, central slice theorem, polar and pseudo-polar Fourier transform, interpolation from a Cartesian coordinate system, and a modified CS solver to be able to recover clinically high quality images from few/low dose projections in a reasonable time. Embodiments described herein may be usable on available CT and MRI scanners. Adapting CS scheme in CT may require a multiplication by a projection matrix, which for a 512×512 image in a scanner with 896 sensors and 1200 projections is (1075200×262144), and its transpose in each iteration. This may make some approaches computationally intense. To reduce the computational complexity, embodiments described herein may assume that the scanned data are on Cartesian or pseudo-polar grids rather than polar grids, on which Fourier transform can easily be computed without interpolation. A description of pseudo-polar can be found at A. Averbuch, R. R. Coifmanb, D. L. Donoho, M. Elad, and M. Israeli, "Fast and accurate polar fourier transform," Appl. Comput. Harmon. Anal., vol. 21, pp. 145-167, 2006, the entire contents of which is hereby incorporated by reference. In fan beam and cone beam CT the acquired data is usually in polar coordinates. Parallel CT may be adjusted in a way to scan data from Equally-sloped (pseudo-polar) grids rather than polar grids. Acquiring data with Cartesian coordinates may not possible in current CT's but may be done in MRI.

Interpolation typically is not feasible for use in iterative algorithms, since it propagates the error in each iteration rather than correcting the error. Embodiments described herein may address the interpolation problem by introducing a confidence matrix which may not only controls the interpolation error propagation, but also may model the poison noise of the CT X-ray projection or complex noise of the MRI data which helps the solver to handle the errors easier.

Embodiments described herein may provide compressed Sensing (CS) based image reconstruction methods and systems which may be used to reduce the X-ray dose radiation in Computed Tomography (CT) and to decrease the scan duration in MR imaging (MRI), for example. Embodiments described herein may address problems that have hindered clinical usage of CS, i.e. computation complexity and modeling problems. Using embodiments described herein, high quality images may be recovered in a reasonable time from undersampled data which may help to reduce the scan time and the exposed invasive radiations. Using the same set of data in conventional image reconstruction algorithms (e.g. FBP in CT) may cause severe streak artifacts and may take more than an hour using Graphics Processing Units (GPU) and parallel clusters with the conventional CS-based methods. Embodiments described herein may be used in any other imaging modalities based on Radon transform (such as C-Arm, electron tomography, for example).

Embodiments described herein may provide methods and systems involving a computational procedure for synthesizing images from scanning data, including CT and MRI procedures. Embodiments described herein may provide methods and systems involving an application of the central slice theorem which may speed up compressed sensing reconstructions (e.g., reconstructions from relatively few projections or view, such as from about 200 views or less) to the point where it was found to take a short time (e.g. less than a minute, 30 seconds, etc.) to reconstruct a CT image (e.g., a 512×512 image) from low-dose, partial data. As a comparison, known computational approaches may be just now nearing the one-hour mark using supercomputers.

Embodiments described herein may provide methods and systems involving a treatment of Poisson noise and interpolation artifacts yielding a Bayesian optimal image estimate. Embodiments described herein may be applicable not only to CT but also to MRI and other suitable tomography techniques where application of the central slice theorem may be used to speed compressed sensing.

Embodiments described herein may provide methods and systems may be used to compute tomographic reconstructions of a specimen from CT, MRI or other scanning data, and which may provide one or more of the following:

Applying the central slice theorem (CST) in a way that may speed up a relatively large class of compressed sensing problems, including those needed to perform full CT compressed sensing reconstructions from incomplete, complete or overcomplete raw observations. In some examples, such as implementation in MRI, use of CST may not be required.

Inclusion of a confidence factor, which may help to increase the effective influence of higher-fidelity observations. The confidence factor may be determined by both observational noise and interpolation uncertainty. This modification to the traditional compressed sensing problem may lead to better noise robustness.

Embodiments described herein may provide methods and systems with one or more of the following:

Using the CST as described herein, certain compressed sensing solvers may perform full CT reconstructions with image sizes of 1024×1024 relatively quickly (e.g., in approximately 4 seconds for a full projection data set having more than 900 projections) on a desktop computer (i.e., not a supercomputer): this may be over four orders of magnitude faster than compressed sensing techniques currently in use.

The confidence measure described herein may improve the noise/dose trade-off (e.g., by about a factor of 10 or more) on a standard sample image.

CT scan dose reductions (e.g., of at least a factor of four) may be achieved while producing diagnostically useful images.

As the described methods and systems allows for undercomplete data collection, super-resolution reconstructions may be possible, with a reasonable computational requirement.

A fast Compressed Sensing based algorithm is described herein to recover clinically applicable (high quality) images from incomplete scan data, desired in MRI to reduce scan duration, or to lower the X-ray dose in CT, C-arm, electron tomography or any other modality in which central slice theorem and direct Fourier recovery is used to recover the images.

Embodiments described herein may be used to recover images from full scan data acquired with low dose CT protocols.

Embodiments described herein may be accelerated by the use of a novel combination of some or all of conebeam and fanbeam to parallel beam rebinning, central slice theorem, Pseudo-polar Fourier transform, and modified compressed sensing solvers, as described herein. Embodiments described herein may provide systems and methods that may be used in the imaging scanners.

Embodiments described herein may use CST or direct Fourier recovery instead of using large matrices (fast algorithms are available to compute the Fourier transform unlike matrix form which is computationally very intensive to be used since it needs two huge matrix multiplications at each iteration) to decrease the computation complexity. To be able to use central slice theorem in the fan beam and cone beam geometries, for which central slice theorem may not be applicable directly, embodiments described herein may use rebinning which rearranges the beams to parallel, for which central slice theorem can be used.

Embodiments described herein may decrease the interpolation error in parallel geometry, and equally sloped scans may be used.

Embodiments described herein may use a confidence matrix to compromise the Poisson noise of the sensors and to control the interpolation error caused by rebinning or by polar to Cartesian or pseudo-polar conversion.

Embodiments described herein may be used in dual energy X-ray CT to reconstruct images from two partial sets of data gathered with different energies to reduce the exposed X-ray dose.

Figure 5:
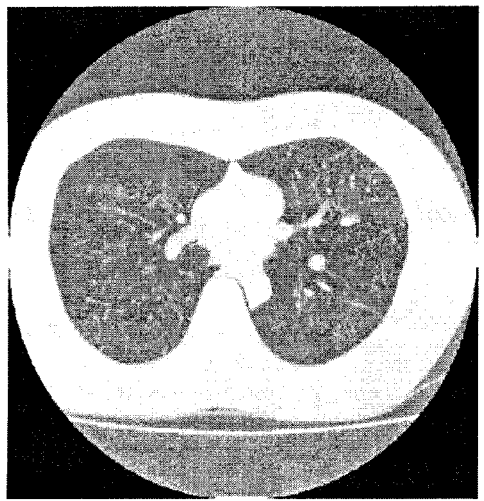
FIG. 5 is an illustrative example of comparison of images including an image generated using FBP and a reconstructed image generated according to compressed sensing image reconstruction according to some embodiments.
Figure 5:
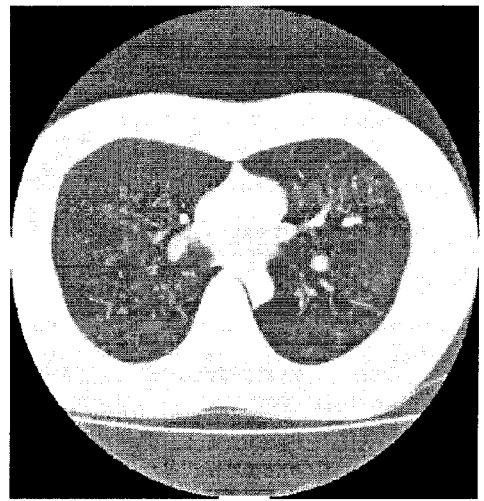

Embodiments described herein may provide tomography reconstruction systems and methods which may address problems in cardiac CT including one or more of limited temporal resolution and radiation dose. In addition to cardiac CTs, embodiments described herein may provide may be applied to compute fast CS reconstructions of MRI data or other tomography modalities. CS, proposed by E. Candès J. Romberg, and T. Tao, "Robust uncertainty principles: Exact signal reconstruction from highly incomplete frequency information," IEEE Trans. Information Theory, 2006; 52:489-509 (the entire contents of which is hereby incorporated by reference), may provide the tools to reconstruct a signal with many unknowns (such as a cardiac CT image) from a smaller number of observations. In general, this task may be difficult or impossible, since one cannot uniquely solve a system of equations with more unknowns than observations. However, if there exists a simple representation of the specimen (such as in the case of a CT image, which may be describable using relatively few simple shapes and contours) such that the number of features of the image is smaller than the number of observations, a CS solver may be used to reconstruct the entire image. Since noise also tends not to possess the same features as the signal, CS may be a way of denoising images (such as is shown in FIG. 5 as will be described herein).

Figure 1:
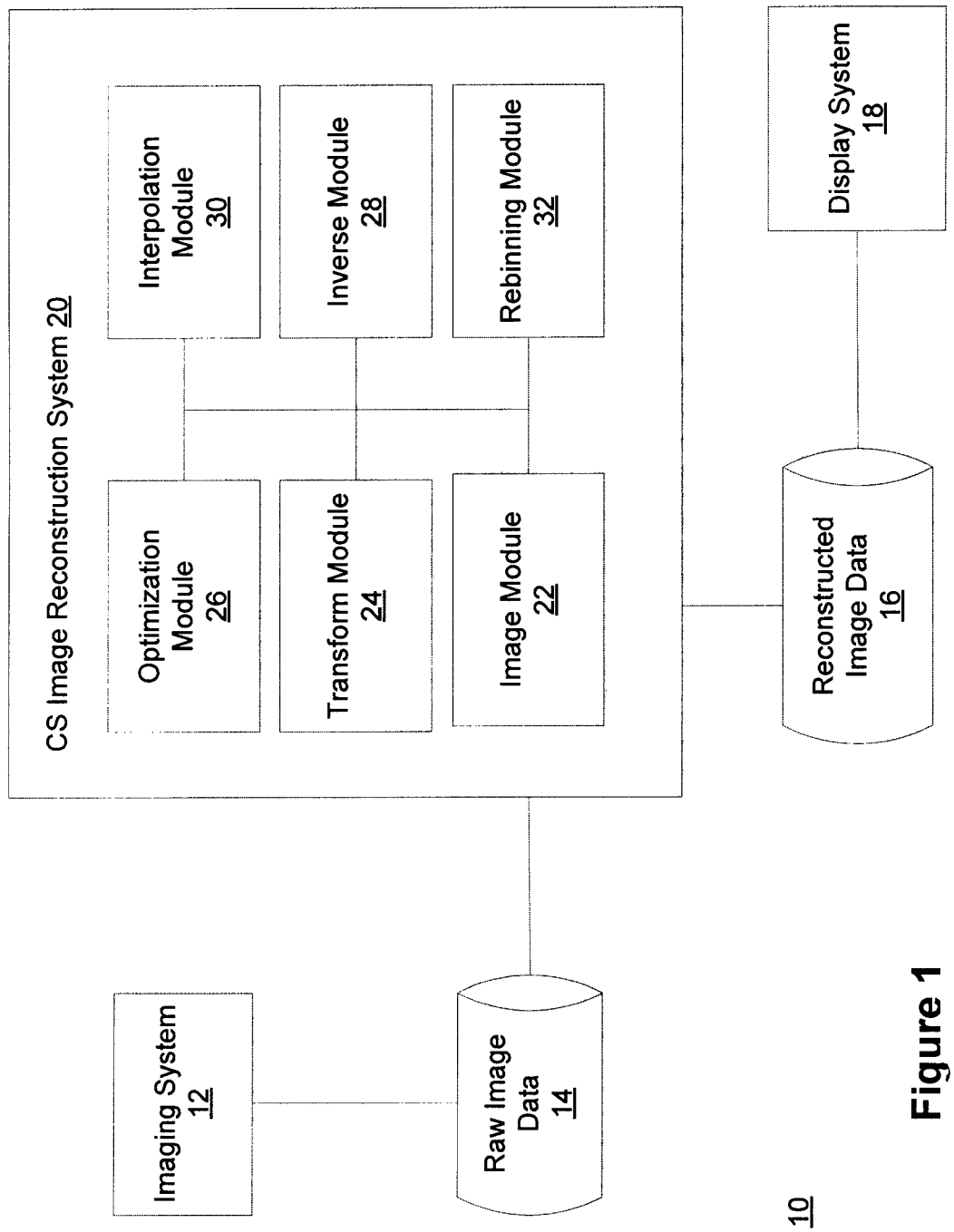
FIG. 1 is a schematic diagram of a system for compressed sensing image reconstruction according to some embodiments.

Referring now to FIG. 1 there is shown a schematic diagram of a system 10 for compressed sensing image reconstruction according to some embodiments.

An imaging system 12 may implement various imaging modalities to generate raw image data 14 using computed tomography (CT) imaging, parallel beam CT scanning, cone beam CT scanning, C-arm scanning, helical CT, scanning magnetic resonance imaging (MRI), electron tomography or other imaging modality. The raw image data 14 may represent various features or parts of a patient under consideration. The raw image data 14 may be in a variety of formats. The raw image data 14 may be incomplete, complete or overcomplete raw image data.

CS image reconstruction system 20 may be implemented using a server (e.g. computing device) and data storage devices configured with database(s) or file system(s), or using multiple servers or groups of servers distributed over a wide geographic area and connected via a network. CS image reconstruction system 20 may have internal data storage devices, may be connected to a data storage device directly or to a cloud based data storage device via network. The data storage devices may store the raw image data 14 for use by CS image reconstruction system 20. CS image reconstruction system 20 may reside on any networked computing device including a processor and memory, such as a personal computer, workstation, server, portable computer, mobile device, personal digital assistant, laptop, tablet, smart phone, WAP phone, an interactive television, video display terminals, gaming consoles, electronic reading device, and portable electronic devices or a combination of these provided CS image reconstruction system 20 has the required processing capabilities to provide CS image reconstruction as described herein. CS image reconstruction system 20 may include one or more microprocessors that may be any type of processor, such as, for example, any type of general-purpose microprocessor or microcontroller, a digital signal processing (DSP) processor, an integrated circuit, a programmable read-only memory (PROM), or any combination thereof. CS image reconstruction system 20 may include any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. CS image reconstruction system 20 may include one or more input devices, such as a keyboard, mouse, camera, touch screen and a microphone, and may also include one or more output devices such as a display screen and a speaker. CS image reconstruction system 20 may have a network interface in order to communicate with other components, to serve an application and other applications, and perform other computing applications by connecting to network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. Although only one CS image reconstruction system 20 is shown for clarity, there may be multiple CS image reconstruction systems 20 or groups of CS image reconstruction systems 20 distributed over a local or wide geographic area and connected via e.g. network.

CS image reconstruction system 20 is operable to generate reconstructed image data 16 for display on display system 18 which may include one or more input devices, such as a keyboard, mouse, camera, touch screen and a microphone, and may also include one or more output devices such as a display screen and a speaker. CS image reconstruction system 20 may be separate from or integral to imaging system 12.

CS image reconstruction system 20 may be configured with various computing applications which may correspond to hardware and software modules comprising computer executable instructions to configure physical hardware to perform various functions and discernible results. A computing application may be a computer software or hardware application designed to perform specific functions, and may include an application plug-in, a widget, instant messaging application, mobile device application, e-mail application, online telephony application, java application, web page, or web object residing, executing, running or rendered on CS image reconstruction system 20. CS image reconstruction system 20 is operable to register and authenticate users (using a login, unique identifier, and password for example) prior to providing access to applications.

Generally, CS image reconstruction system 20 may include an image data module 22 operable to receive signals representing a set of raw image data 14. A transform module is operable to perform a 1-dimensional Fourier transform on the set of raw image data to convert the set of raw image data into a partial Fourier domain. An optimization module is operable to determine a set of reconstructed image data from the set of raw image data in the partial Fourier domain, based on an optimization model. An inverse module is operable to perform an inverse operation on the set of reconstructed or recovered image data to convert the set of reconstructed image data into an image domain. The image module is further operable to generate signals representing the set of reconstructed image data 16. As noted herein, an imaging workstation 12 is operable to generate the raw image data 14 from scans of a patient and a display system 18 is operable to display the set of reconstructed or recovered image data 16 as a reconstructed or recovered image.

In some example embodiments, CS image reconstruction system 20 may further include an interpolation module 30 for determining an interpolation of the set of raw image data in the Fourier domain from a polar coordinate system to a pseudo-polar or Cartesian coordinate system.

In some example embodiments, the set of raw image data 14 is based on non-parallel beam geometries, and CS image reconstruction system 20 may further include a rebinning module 32 for rebinning the set of raw image data based on parallel beam geometries.

In some example embodiments, the imaging system 12 may an MRI imaging system. In such case, the raw image data 14 may not be required to be processed by the transform module 24 and may be processed directly by the optimization module 26 once received at the image module 22.

Figure 2:
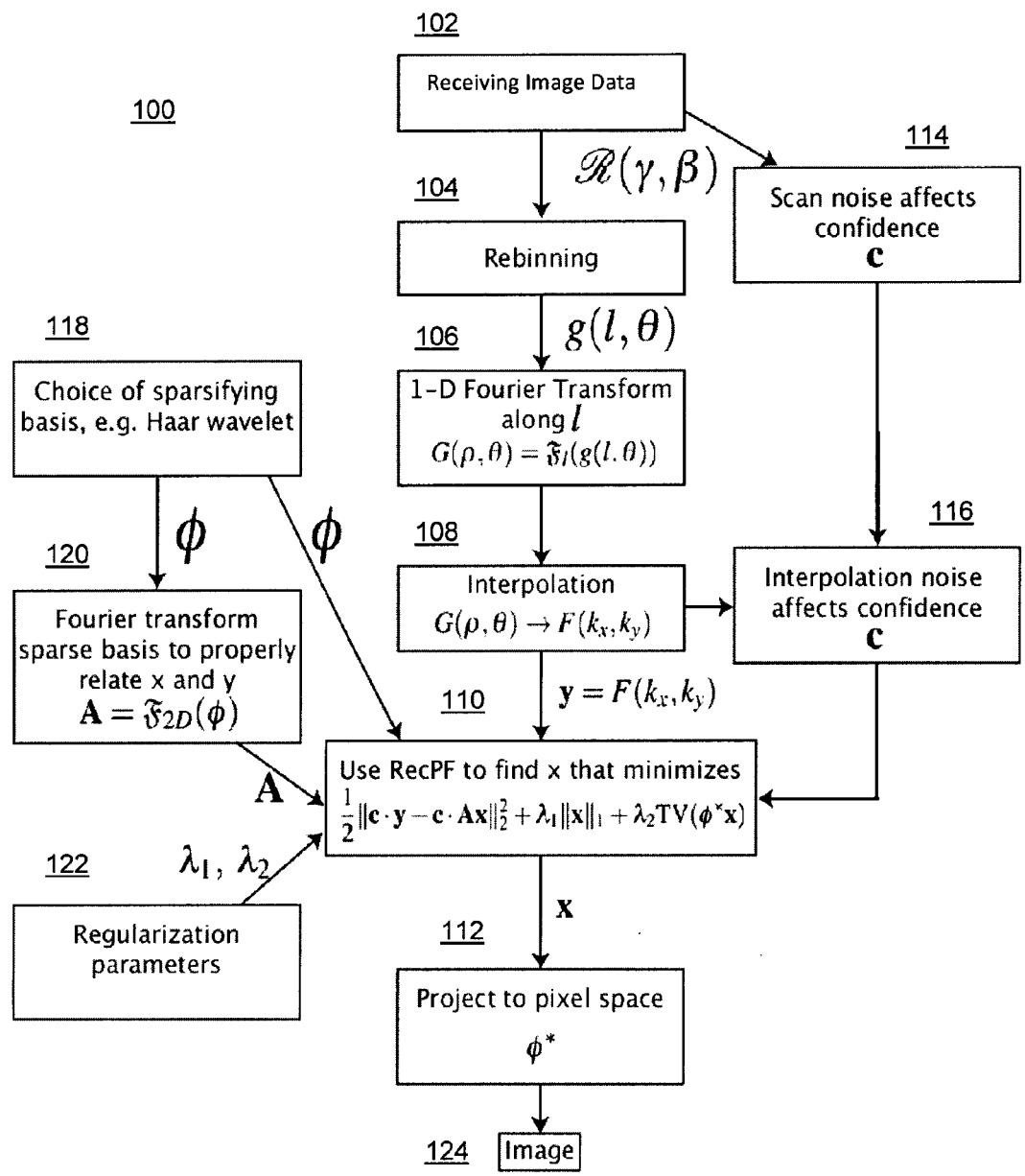
FIG. 2 is a flow chart diagram of a method for compressed sensing image reconstruction according to some embodiments.
Figure 3:
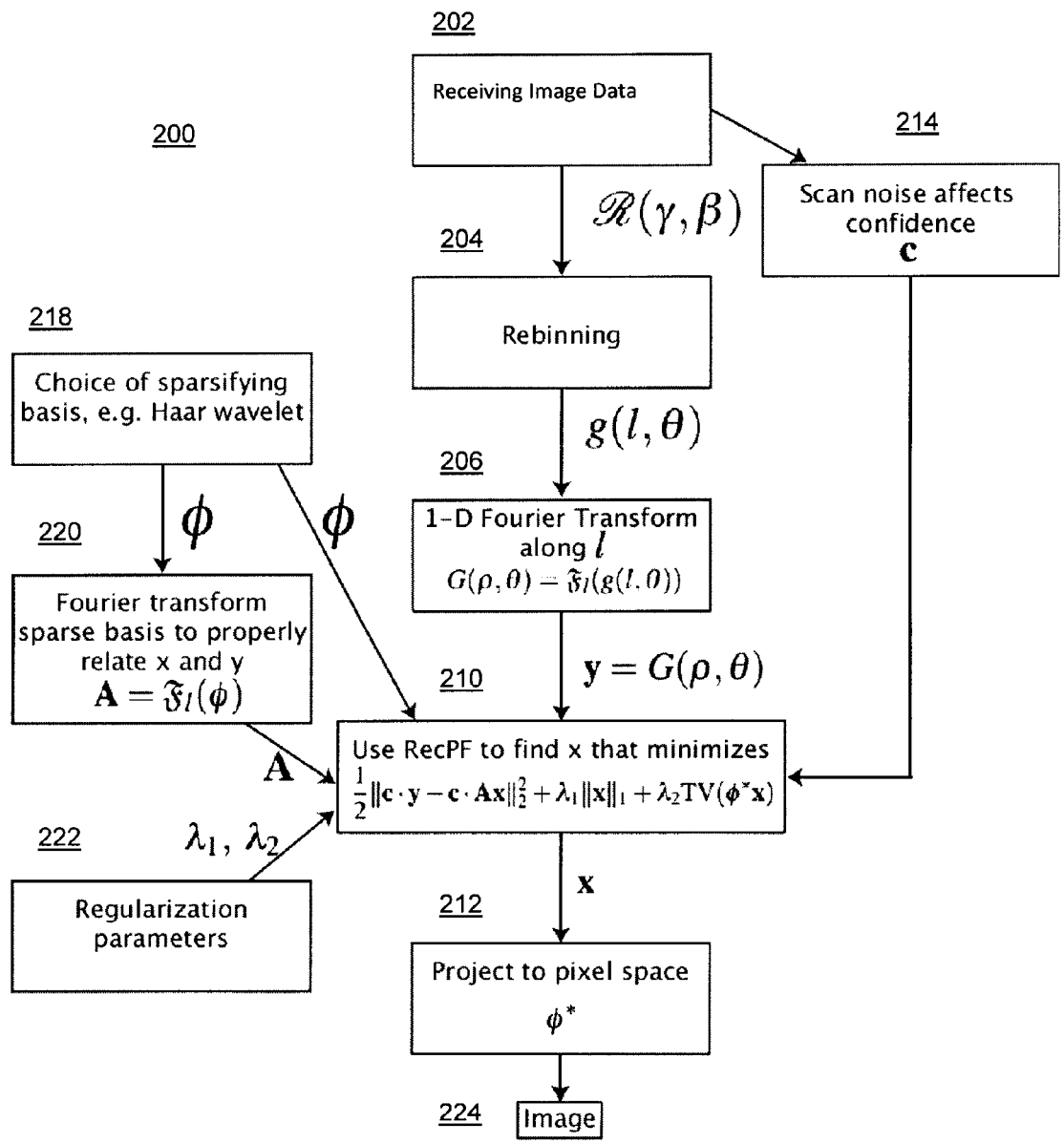
FIG. 3 is a flow chart diagram of another method for compressed sensing image reconstruction according to some embodiments.
Figure 4:
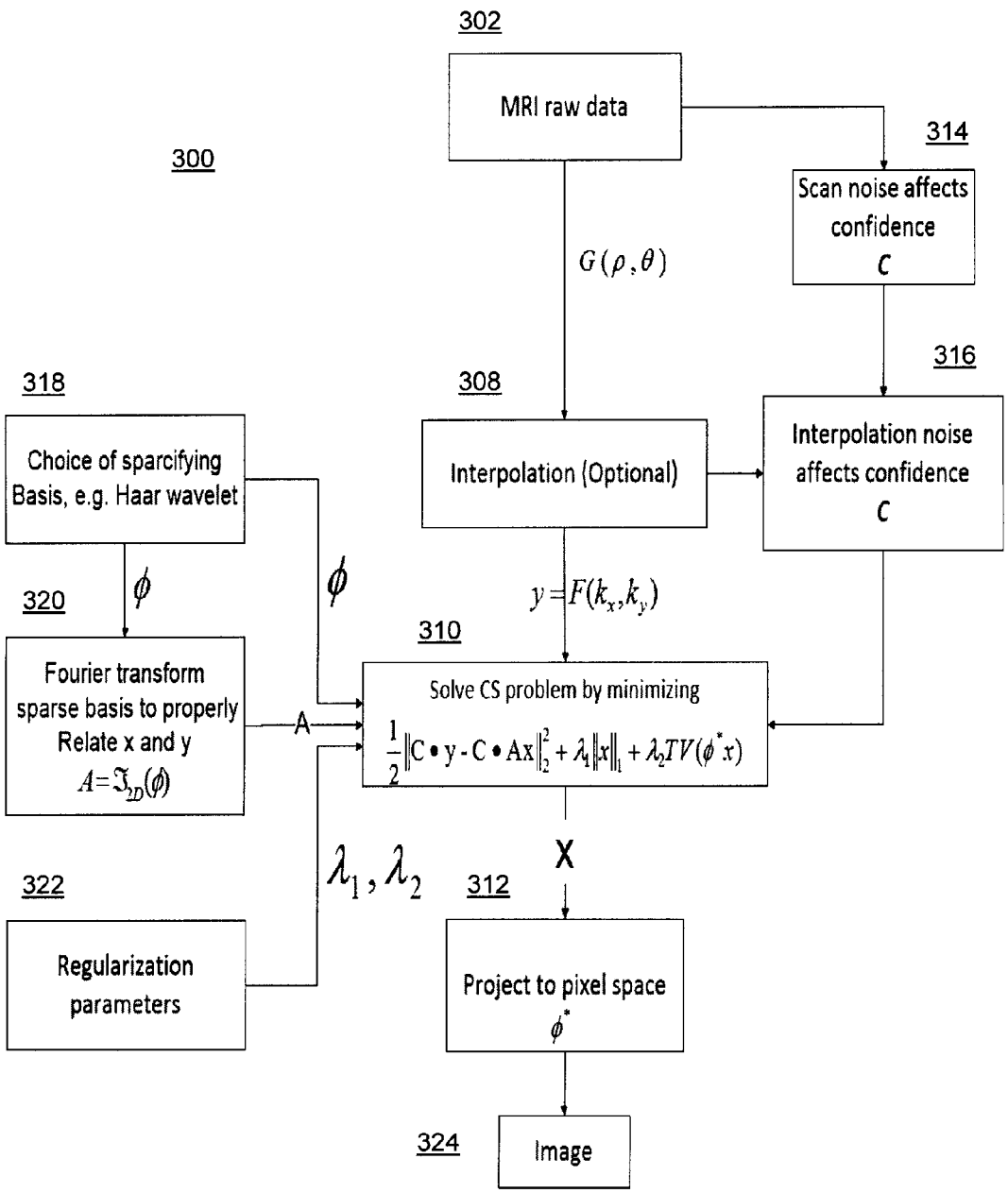
FIG. 4 is a flow chart diagram of further method for compressed sensing image reconstruction according to some embodiments.

Referring now to FIGS. 2, 3, and 4 there is shown a flow chart diagram of methods 100, 200, 300 for compressed sensing image reconstruction according to some embodiments. FIGS. 2 and 3 are example methods 100, 200 where an imaging system 12 implements CT imaging, parallel beam CT scanning, cone beam CT scanning, C-arm scanning, helical CT, electron tomography or other imaging modality. FIGS. 2, 3, and 4 provide an overview of example implementations of embodiments described herein. Various terms and equations used are defined later herein. FIG. 2 shows a flowchart describing an example CT scan implementation of the disclosure, where polar Fourier data is interpolated onto a 2D Cartesian Fourier space. FIG. 3 is a flowchart showing another example computation of an image using an example of the present disclosure. In this example, a CT-derived image is computed using pseudo-polar coordinate Fourier coefficients directly (i.e., without interpolation from pseudo-polar coordinate system to Cartesian coordinate system). FIG. 4 is an example method 300 where an imaging system 12 implements MRI. The steps are not typical in compressed sensing reconstruction, possibly because the computational burden of compressed sensing using current methods is overwhelming.

In the examples of FIGS. 2, 3, and 4 solving a CS problem in the Fourier domain, rather than the Real domain (e.g., image space) may help to simplify and/or speed up the optimization problem. This may be due to a decrease in the mutual-coherence of noise contributions, for example. In these examples, CS may be used to reconstruct image data from sparse or incomplete image data. Other techniques may be used.

At 102, 202, 302, image module 22 receives signals representing a set of raw image data 14. As noted, at 302, the raw image data 14 is generated from MRI. In FIG. 2 raw data may generate fan-beam observations $\Re(\gamma,\beta)$. A 1-D Fourier transform of the data along l is taken; exploiting the central slice theorem.

In accordance with some embodiments, at 104, 204. The rebinning module 32 is operable to rebin the raw image data 14 based on parallel beam geometries. The data may be rebinned to mimic a parallel beam geometry $g(l,\theta)$.

At 106, 206, the transform module 24 performs a 1-dimensional Fourier transform on the set of raw image data 14 to convert the set of raw image data into a partial Fourier domain.

In accordance with some embodiments, at 108, 308, interpolation to a rectangular Fourier domain $G(\rho,\theta) \rightarrow F(k_x,k_y)$ may be carried out. Such techniques typically have not been used in currently CT reconstruction.

In the example of FIG. 3, the interpolation between polar and rectangular Fourier transforms may be avoided by working directly in the polar Fourier basis. This may be useful where the raw image data is in the polar coordinate system (e.g., as in the case of CT).

In accordance with some embodiments, at 110, 210, 310, optimization module 26 determines a set of reconstructed image data from the set of raw image data in the partial Fourier domain, based on an optimization model. The optimization model used in these examples may be RecPF, however any other suitable optimization model/algorithm may be used.

The application of a compressed sensing solver (in this example, the RecPF optimization algorithm) directly in the Fourier domain may be used to find an image compatible with both the data and with a sparsity assumption. The matrix A may incorporate the necessary Fourier transform directly, as well as a sparsifying basis. The confidence measure may be influenced by interpolation noise artifacts. See for example, G. Besson, "CT image reconstruction from fan-parallel data," Med. Phys., 1999; 26, 415-426, the entire contents of which is hereby incorporated by reference. Acting in the Fourier domain may reduce the mutual coherence between columns of A, and incorporating the Fourier transform directly in A may help to avoid the need to perform any Fourier transformation during the actual compressed sensing computation. Both of these effects together may speed up CT scan calculations by many orders of magnitude.

At 112, 212, 312, inverse module 28 performs an inverse operation on the set of reconstructed image data to convert the set of reconstructed or recovered image data into an image domain. Inverse module 28 is operable to project the recovered image data to pixel space, for example.

At 124, 224, 324, image module generates signals representing the set of reconstructed image data 16, which may be displayed by display system 18 as a reconstructed image.

In some examples, at 114, 116, 214, 314, 316 information about the Poisson noise associated with the measurement may be factored into confidence associated with each data point. Accounting for noise resulting from the interpolation from the polar coordinate system to the Cartesian coordinate system (e.g., as shown in FIG. 2) may be based on applying a weighting to each data point in the Cartesian coordinate system, based on a known amount of confidence in interpolation between the polar coordinate system and the Cartesian coordinate system, for example.

In some examples, at 118, 120, 218, 220, the image may be assumed to be sparse in some basis, in this example the Haar wavelet basis $\phi$ is used as the set of sparse data for reconstructing the image. Compressed sensing solvers seek a solution that is sparse in this basis yet consistent with data. Other basis data may be used including, for example, other types of wavelets, (e.g., Gabor wavelet, Daubechies wavelet), curvelet or any other sparsifying transform. In some examples, the CS Image reconstruction system 20 may have access to a wavelet "dictionary", for example a database of different wavelets, from which one or more suitable wavelets may be selected as the basis data. In some examples, the basis data may include one or more non-wavelets. The selection of the appropriate wavelet(s) and/or non-wavelet(s) may be based on prior knowledge of the expected reconstructed or recovered image data. The calculation $A=\mathfrak{S}_1(\phi)$ to find the polar Fourier representation of the wavelet basis may be computationally intense, but may be required only once, may be performed offline before scan data is acquired, and may be applicable to any fixed wavelet basis $\phi$. The use of polar Fourier transform may be uncommon.

The use of rebinning and accounting for noise (e.g., scan noise and/or interpolation noise) is included as an illustrative example. However, in other examples one or more of these steps may be excluded.

In some examples, at 122, 222, 322, regularization parameter(s) may be user-specified parameter(s) and/or preset parameter(s). For example, a user-specified regularization parameter may define how much weight should be placed on prior knowledge of the expected reconstruction compared to fidelity to the raw image data. Accordingly, in addition to basis data, one or more regularization parameters may be received as input by CS Image Reconstruction System 20 for solving CS.

FIG. 5 is an illustrative example of comparison of images including an image generated using FBP and a reconstructed image generated according to compressed sensing image reconstruction according to some embodiments. That is, FIG. 5 shows a comparison of reconstructions based on a noisy dataset. Filtered back projection (FBP) (see equation (3) herein) was found to yield a noisy image 402, while compressed sensing image 404 (see equation (7)) was found to reject more noise artifacts. The signal-to-noise ratio (SNR) of the image reconstructed by FBP was found to be 20 dB and SNR of the image reconstructed by the proposed method was found to be 29.4 dB. Both images 402, 404 in this example used 500 views.

In some examples, the embodiments described herein provide methods and systems of applying the CST with compressed sensing which may offer improvements in cases where incomplete, complete or overcomplete data is available and the clinician desires a sparse representation of the specimen based on a CT, MRI or other tomography technique. Examples of these scenarios include the desire to denoise a specimen, to obtain superresolution, to make any quantitative measurement that may or may not include forming a specimen image, to narrow diagnostic focus to a specific region of interest using computational or physical means, to reduce scan dose, time or cost, to reduce computation cost, or any scenario in which a convex or non-convex numerical problem solver may be employed to discover one or many images or non-image observations that are both consistent with observations and with prior expectations of the statistics of the spatial distribution of any type of feature in the specimen.

Embodiments described herein provide an example of the utility of the disclosed technique. Using CS and a dedicated reconstruction algorithm, it was possible in the example to reconstruct a clinically acceptable image from simulated CT data using fewer projections from a smaller than standard gantry rotation angle (i.e. less than a 180° fan beam angle needed in conventional reconstructions). This supports the use of embodiments described herein provide to address CT limitations of gantry rotation that may not be sufficiently fast (e.g., 1 cycle in 0.3 s or slower) and cardiac motion by improving in-plane temporal resolution, as significantly fewer data projections may be required to form an image.

CS may be used to cope with incomplete data and high noise. However, CS may be difficult to scale up to practical use for reconstructing images of a practical size (e.g., CT or MRI images). For example, current CS implementations may be much more computationally expensive than FBP—the current standard CT algorithm (see equations herein)—and standard MRI reconstruction techniques.

Figure 6:
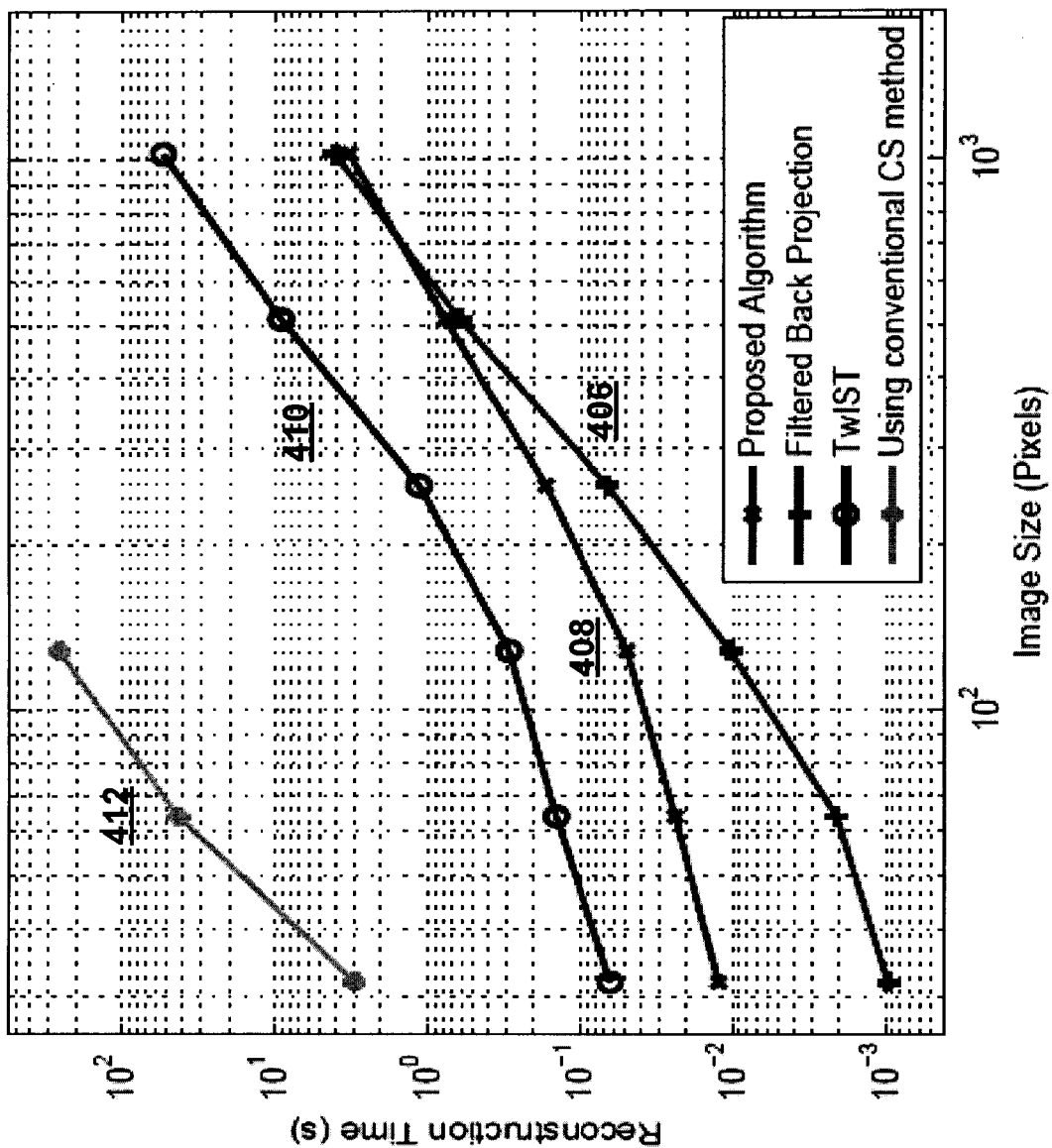
FIG. 6 illustrates example reconstruction times of various alternative CT reconstruction algorithms as a function image size.

FIG. 6 illustrates example reconstruction times of various alternative CT reconstruction algorithms as a function image size. FIG. 6 compares the reconstruction time for CT computations using:

1. FBP (line 406);
2. an example of the embodiments described herein (line 408);
3. two stage iterative reconstruction (TwIST) (see for example J. M. Bioucas-Dias and M. A. T. Figueiredo, "A New TwIST: Two-Step Iterative Shrinkage/Thresholding Algorithms for Image Restoration," IEEE Transactions on Image Processing, 2007; 16(12): 2992-3004) (line 410); and
4. CS with forward and backward projections (a conventional CS reconstruction method) (line 412).

As can be seen using Matlab implementations of the algorithms, in terms of computation time, the example of the embodiments described herein compares well with FBP.

FIG. 6 shows example reconstruction times of various alternative CT reconstruction algorithms as a function of image size. Conventional, full CS techniques may be currently computationally impractical for medically-relevant image sizes. Conventional iterative reconstruction methods typically face this difficulty (see for example, H. K. Bruder, R. Raupach, M. Sedlmair, J. Sunnegardh, K. Stierstorfer, and T. Flohr. Adaptive iterative reconstruction (AIR). In spie-7691, page 76910J, 2011, the entire contents of which is hereby incorporated by reference). In contrast, for large images, CS image reconstruction system 20 may compute full CS solutions in a relatively short amount of time (e.g., a few seconds) using examples described herein.

In various examples, computational time information for CT scans are provided to illustrate example embodiments, however such examples and time information are illustrative only and should not be considered limiting or characterizing embodiments described herein. Although CT is discussed as one example implementation of the present disclosure, the present disclosure may be applicable to MRI and other tomography methods and to any other technique (not limited to CS) that seeks images in accordance both with observations and with preconceived or discovered mathematical or physiological assumptions regarding the probable nature of the specimen.

The presently disclosed methods and systems may perform one or more of:

1. Calculate expected noise values from knowledge of the measuring device's physics. For example, with CT scans, the photon count may influence Poisson noise levels in raw scanner measurements.
2. Convert the scan geometry into a format compatible with the Central Slice Theorem (CST). For example, in modern CT scans, fanbeam geometry typically must be converted to parallel geometry (see below). In some examples that may be implemented in MRI, use of CST may not be necessary.
3. Interpolate polar data to a rectangular coordinate system (i.e., a Cartesian coordinate system) if necessary, as required by the CST (see for example, H. Stark, J. Woods, I. Paul, and R. Hingorani. "Direct Fourier Reconstruction in Computer Tomography," IEEE Transactions on Acoustics, Speech, and Signal Processing, 1981; 29(2): 237-45, the entire contents of which is hereby incorporated by reference). This step may be required by some CT scanning, but may be optional in others (e.g., as in the example of FIG. 3), may or may not be required by MRI (e.g., depending on whether or not a polar coordinate Fourier transfer is used, such as is shown in FIG. 4 as being optional), and may or may not be required by other tomographic techniques depending on their geometry.
4. Use the CST to perform data fitting (e.g., using CS or an alternative technique) in this alternative space, which typically decreases the problem's coherence, speeding CS or its alternative. Additionally, computations in this space typically do not require computationally costly transformations between specimen feature space and the space of the natural or transformed scan data.
5. Use a compressed sensing based recovery algorithm or an alternative to recover images of relatively high accuracy and quality from incomplete, complete or overcomplete raw image data.
6. Project back into image space for imaging, or alternatively projects into a measurement basis to perform the desired measurement when non-imaging results are desired.

Embodiments described herein provide systems, methods, techniques and algorithms that may be implemented by a processor of a system (e.g., an imaging system 12, or CS image reconstruction system 20). The processor may be coupled to one or more internal and/or external memories that may store instructions for carrying out various functions and processes, including instructions for carrying out the methods, techniques and algorithms disclosed herein. The data storage devices may also include one or more databases. The processor may receive signals representing raw image data 14 and may perform calculations and transformations on such data in order to generate signals representing reconstructed image data 16. Such generated signals may be used to display the reconstructed or recovered image data (e.g., as a reconstructed image on a screen of an imaging workstation), stored for later access and/or transmitted to an external system for storage and/or further processing, and/or display (e.g. display system 18).

Details of the example methods 100, 200, 300 used in the examples of FIGS. 2, 3 and 4 are now described.

Filtered Back Projection—Review and History

Herein is described one example of the type of transformation that may be needed to project data into a space where the central slice theorem may act. In CT, the raw data acquired may be the number of photons which hit the detectors in different angles (see for example, G. T. Herman, Fundamentals of Computerized Tomography: Image Reconstruction from Projections, 2nd edition, Springer, 2009, the entire contents of which is hereby incorporated by reference). For parallel beam geometry the projections can be expressed as the Radon transform of the object. The Radon transform is defined as (see for example S. R. Deans, The Radon Transform and Some of Its Applications, New York, John Wiley & Sons, 1983, the entire contents of which is hereby incorporated by reference):

$$g(l,\theta) = \mathcal{R}(f) = \int_{-\infty}^{\infty}\int_{-\infty}^{\infty} f(x,y)\delta(x\cos\theta + y\sin\theta - l)dxdy \quad (1)$$

which is the integral along a ray at angle $\theta$ and at the distance of $l$ from the origin.

Figure 7:
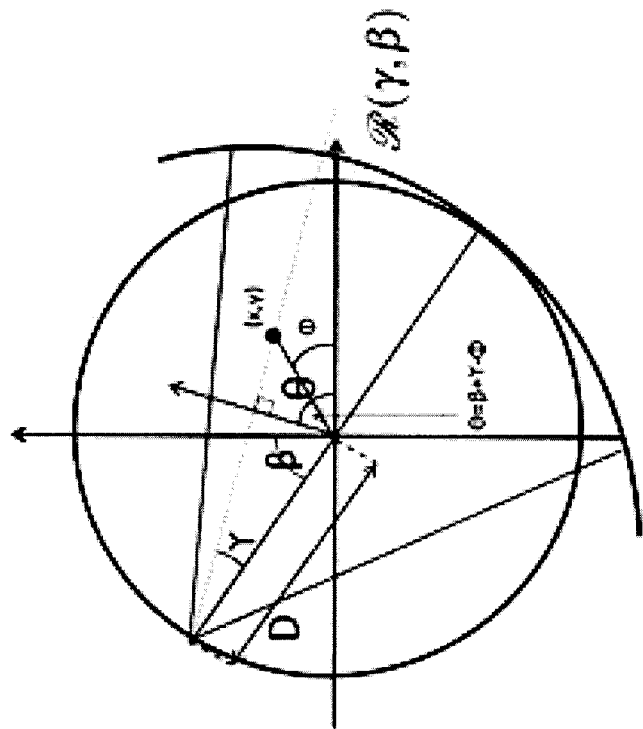
FIGS. 7 and 8 illustrate examples of fan beam geometry.
Figure 7:
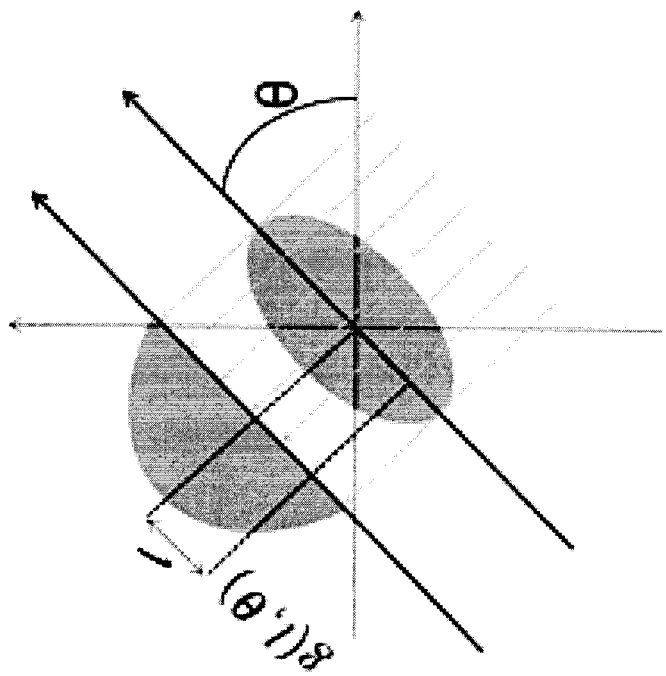
Figure 8:
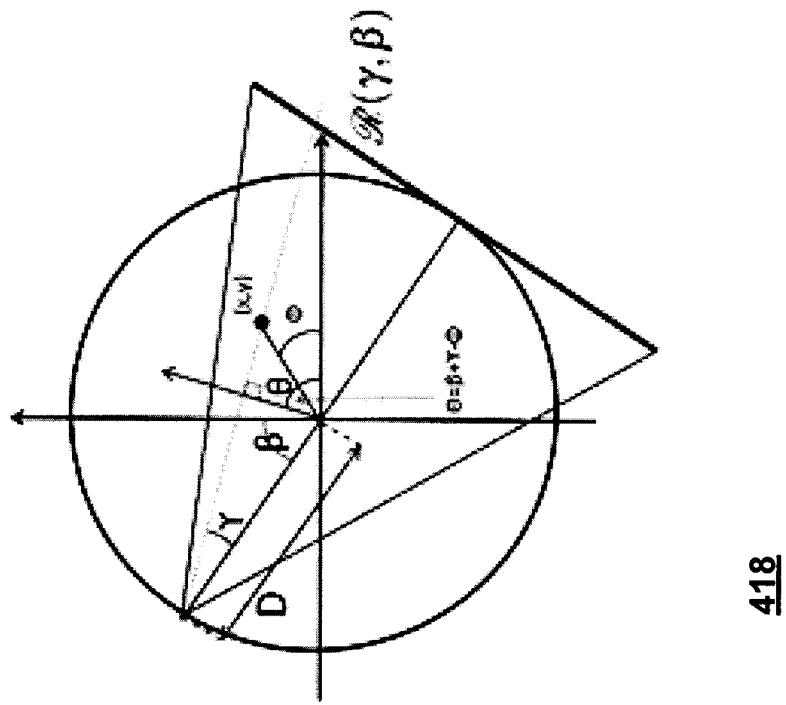
Figure 8:
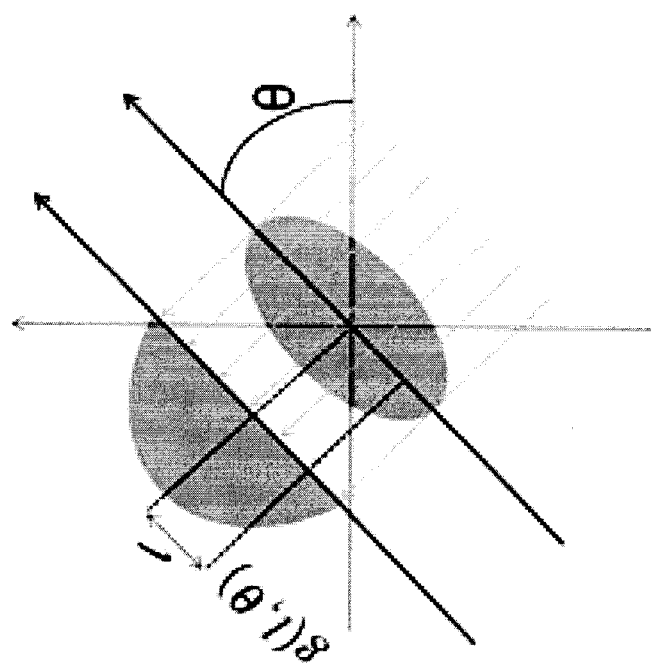

However, current CTs typically use fan beam tomography rather than parallel tomography which can be easily modeled by considering the fan beam geometry shown in FIGS. 7 and 8 and using the geometry in (1):

$$\mathcal{R}(\gamma, \beta) = g(D\sin\gamma, \beta + \gamma) \quad (2)$$

$$l = D\sin\gamma, \theta = \beta + \gamma, \gamma_{min} = -\sin^{-1}\frac{\tau}{D}, l = D\sin\gamma$$

To construct an image of the specimen, it is necessary to solve an inverse problem that inverts (2) or (1) to recover f(x,y). The inverse problem of (1) is known as the inverse radon transform or Filtered Back Projection (FBP):

$$\tilde{f}(x,y) = \int_0^\pi g(x\cos\theta + y\sin\theta, \theta)d\theta \quad (3)$$

In digital images Back Projection may be considered equivalent to calculating the sum of all rays in different angles that pass through a single pixel. The inverse transform of (2) may be similar to the parallel geometry but each detector signal at position γ is scaled by cos γ and each reconstructed position (x,y) is scaled by $$\frac{1}{D'^2}: \tilde{f}(x,y) = \int_0^{2\pi}\frac{1}{D'(\beta)^2}\int_{\gamma min}^{\gamma max}\cos\gamma g(\gamma, g)d\gamma d\beta \quad (4)$$

When the observed data is complete and noiseless, FBP yields f(x,y) exactly. However, in real applications, noise and finite sampling typically cause the solution from (4) to depart from f(x,y).

FIGS. 7 and 8 illustrates: Parallel beam geometry 412, 416, and Fan beam geometry 414, 418.

Alternative Scan Protocols

The previous section may be applicable to fan-beam CT, however the present disclosure may be applicable to various alternatives. The embodiments described herein may also apply to any other configuration or arrangement of CT, MRI or other tomographic data where transformations may be made into a space where the central slice theorem is applicable so as to permit a fast compressed sensing or other solver in conjunction with the central slice theorem. Such alternatives may include the following techniques and their variants, for example: parallel beam CT scanning, cone beam CT scanning, C-arm scanning and helical CT scanning.

The Central Slice Theorem

Embodiments described herein may provide for relatively fast and accurate CS or other reconstructions with tomography problems through the application of the Central Slice Theorem. The Central Slice Theorem (see for example [14] D. Gottlieb, B. Gustafsson, and P. Forssen, "On the Direct Fourier Method for Computer Tomography," IEEE Transactions on Medical Imaging, 2000; 19:223-232, the entire contents of which is hereby incorporate by reference) derives the relationship between the 1D Fourier transform of the projections in different angles and the 2D Fourier transform of f(x, y), the desired image. As in (5), for parallel beam geometry and ignoring limitations due to finite sampling, the 1D Fourier transform of each projection equals the 2D Fourier coefficients of the object along a line that passes through the center of the frequency domain with the same angle as the corresponded projection. Therefore, this method can be used as an alternative to reconstruct the CT images by computing the 1D Fourier coefficients of the projection and (optionally) putting them along the corresponding line in the 2D Fourier domain, and finally taking the inverse 2D Fourier transform of the interpolated result. The Central Slice Theorem can be derived as per the following:

$$f(x,y) = \int_{-\infty}^{\infty}\int_{-\infty}^{\infty}F(k_x,k_y)e^{+j2\pi(k_x\times x + k_y\times y)}dk_x dk_y \quad (5)$$

$$= \int_0^{2\pi}\int_0^{\infty}F(\rho\cos\theta, \rho\sin\theta)e^{+j2\pi\rho(x\cos\theta+y\sin\theta)}\rho d\rho d\theta$$

$$= \int_0^{2\pi}\int_0^{\infty}G(\rho,\theta)e^{+j2\pi\rho(x\cos\theta+y\sin\theta)}\rho d\rho d\theta$$

$$= \int_0^{2\pi}\left[\int_0^{\infty}|\rho|G(\rho,\theta)e^{+j2\pi\rho l}d\rho\right]_{l=x\cos\theta+y\sin\theta}d\theta$$

$$f(x,y) = \int_0^\pi \mathfrak{I}_{1D}^{-1}\{|\rho|G(\rho,\theta)\}_{l=x\cos\theta+y\sin\theta}d\theta$$

where $F(k_x,k_y)$ is the 2D Fourier transform of the image, and $G(\rho,\theta)$ is the 1D Fourier transform of a projection with distance E from center and angle θ. This method is exact in limit where f(x,y) becomes effectively continuous compared to the sampling density. However, in reality scans typically cannot be ideally continuous, and the number of projections typically is also finite. In MRI as well, acquired data are typically finite. Thus, to be able to reconstruct an image, an interpolation may be done to translate between $G(\rho,\theta)$ and $F(\rho\cos\theta, \rho\sin\theta)$ (but see FIG. 3 for an example implementation that avoids interpolation). Interpolation should be performed carefully to help minimize artifacts, and the accuracy of interpolated coefficients (and thus the confidence measure—see below) typically depends on the proximity of an interpolated $F(k_x,k_y)$ to the nearest available measured point. In addition, as can be seen in (5) the |ρ| term typically limits the band of spatial frequencies available, another possible source of discrepancy with the ideal CST-based reconstructions. The limitations based on finite spatial frequency and sampling density for CST reconstruction may be comparable to those of FBP and traditional MRI reconstructions; the one additional potential source of error for fan beam CT scans and tomography with similar geometry may be in interpolations between polar and rectangular coordinates, which has been accomplished before and may be improved upon (e.g., by adjusting the confidence in any particular interpolated value).

For helical, cone-beam, and C-arm CT scanning, and MRI or alternative tomography methods where an additional degree of interpolation may be performed along one or more dimensions, the confidence measure associated with an interpolated actual or synthetic measurement may depend on its proximity to an actual measurement. In the case where another data redistribution is required (such as in the conversion of fan beam to parallel beam CT imaging), additional factors may influence the confidence measure. For example, example implementations of the present disclosure may include compensations for rebinned data (see below) close to the edge of available measurements when a limited number of angles are available (e.g. near the edges of acquired data in FIG. 9).

Rebinning

A way to perform CT fan beam reconstruction may be to redistribute data from a fan beam geometry to a parallel beam geometry. This redistribution may enable parallel reconstruction methods (e.g. Filtered Back Projection and the Central Slice Theorem) to be used with techniques that may otherwise require parallel geometry. This type of method is called rebinning.

Compressed Sensing

Since the overall X-ray radiation dose is equal to radiation at each view×number of views, one of the potential ways to reduce the dose is to reduce the number of views. Moreover, in a patient with a quickly-beating heart, the number of views available may be reduced. Using FBP (and reconstructions that take the FBP image as a starting point, such as the currently clinically used iterative reconstruction methods) to reconstruct the image from under-sampled data typically introduces severe streak artifacts as seen in FIG. 9.

Figure 9:
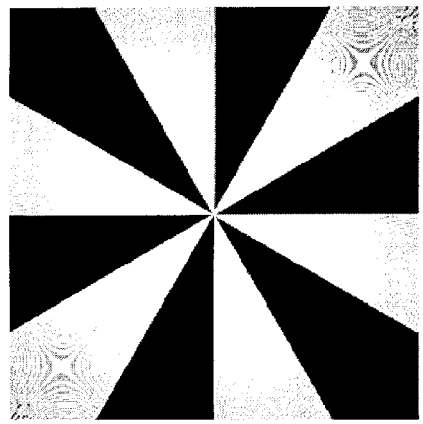
FIG. 9 is another illustrative example of comparison of images including an image generated using FBP and a reconstructed image generated according to compressed sensing image reconstruction according to some embodiments.
Figure 9:
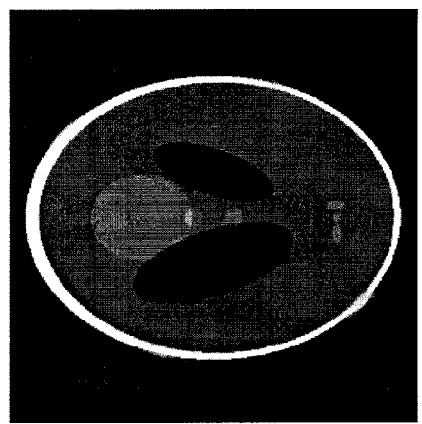
Figure 9:
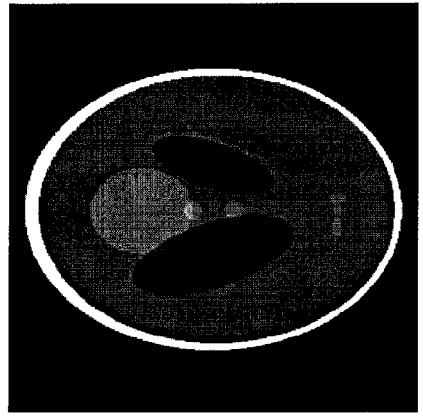
Figure 9:

FIG. 9 shows example comparisons of FBP and CS reconstructions given a CT data set acquired with incomplete angle information. Top right: each line represents an angle at which a scan took place (image 420). Bottom-left: FBP typically does not cope well with incomplete data (image 426). Bottom-right: an example of the embodiments described herein using the CS technique was found to yield a much better reconstruction (image 422), in view of the original (image 424).

In some aspects, the embodiments described herein use CS to reconstruct the image from relatively few views. CS-based reconstruction methods may be able to reconstruct the exact image from relatively few views compared to those needed in FBP (e.g., approximately one tenth of those needed in FBP), which may be much less than the number of views that conventional iterative reconstructions typically handle. To be able to recover images with this few number of views, CS exploits the fact that the specimen is known to be describable using only a few features.

Embodiments described herein may allow for the selection of one of several techniques related to compressed sensing. In its most general application, embodiments described herein may apply to any use of a mathematical solver in the basis arrived at through the central slice theorem to yield an image or measurement in less computational time than would be required without using the central slice theorem.

Currently, CS is an excellent such choice, and it is described below as a sample implementation of the present disclosure. This example uses an optimization paradigm called basis pursuit denoising (BPDN), an optimization problem associated with CS, to determine which features should be present, in what magnitude. BPDN is defined as:

$$\operatorname*{argmin}_{x} \frac{1}{2} \|y - Ax\|_2^2 + \lambda \|x\|_1 \quad (6)$$

where x is the sparse representation of the image, y is the measured data from all the projections, Ax is the expected data given a hypothetical specimen x, and λ is a regularization parameter specifying the denoising trade-off between sparsity and fidelity to observations. Augmenting (6) with a second regularizer $\lambda_2 TV(\phi^* x)$ to decrease the incidence of spatially-localized small fluctuations for which there is little observational evidence, the result is the CS optimization problem used in various examples of the present

DISCLOSURE $$\operatorname*{argmin}_{x} \frac{1}{2} \|y - Ax\|_2^2 + \lambda_1 \|x\|_1 + \lambda_2 TV(\phi * x) \quad (7)$$

where $\phi^* x = f$ is the reconstructed image and TV is the total variation norm, namely $Tv(f) = \Sigma(|\nabla_x f| + |\nabla_y f|)$ where $\nabla_x f$ and $\nabla_y f$ are the discrete image gradients in the x and y directions correspondingly. In the case of CT scans with incomplete data, the measurements y are the partial Fourier transform of the image ($\Im_p \times f$) which are taken from the interpolated 1D Fourier transform of the projections which, using the CST, are equivalent to the partial 2D Fourier coefficients of the image f. Alternatively, y can be the coefficients of $G(\rho,\theta)$ directly, once a corresponding A has been computed (see FIG. 3). Spatial sparsity is encouraged by the measurement matrix $A=\Im_p \times \phi^*$. $\phi$ is the transform which is used to sparsify the image, e.g. a Haar discrete wavelet transform, and * is the conjugate transpose operator. Individual columns of A thus represent sparse specimen features, and a sparse x that can explain the data while keeping TV small is sought.

To solve (7), an L1, L2, TV optimization problem, the RecPF (see for example J. Yang, Y. Zhang and W. Yin, "A Fast Alternating Direction Method for TVL1-L2 signal reconstruction from Partial Fourier Data," IEEE Journal of Selected Topics in Signal Processing Special Issue on Compressed Sensing, 2010; 4(2): 288-297, the entire contents of which is hereby incorporated by reference) algorithm may be used, although other methods can be used, including but not limited to SPGL1, FPC, homotopy, in-crowd, GPSR, CoSAMP, AMP and their variations—see http://goo.gl/LZ4s0 Compressive Sensing for a partial list of CS solvers with over 100 entries. In addition, other regularization methods and terms or combinations thereof may be used in this solution, including convex ones such as any combination of elastic net, $L_p$ norms with 1≤p, or Dantzig selectors and non-convex ones such as smooth-L0 norms, $L_p$ norms with 0≤p<1, Kolmogorov complexity (or a convex or non-convex approximation thereof), model-based priors built on underlying structural assumptions or any other regularization term.

The TV regularization term may help smooth the image at the possible risk of loosing some small features. $\lambda_2$ may be adjusted in a manner that makes good clinical sense. For example, in cardiac CT it may not be necessary to look for ground glass opacities found in the lung, $\lambda_2$ may be increased to remove noise, lowering the required radiation dose. Similarly, the present disclosure may include the option of any combination of any regularizer applied with any strength to a tomography inverse problem where the central slice theorem may be used to speed computations.

Figure 10:
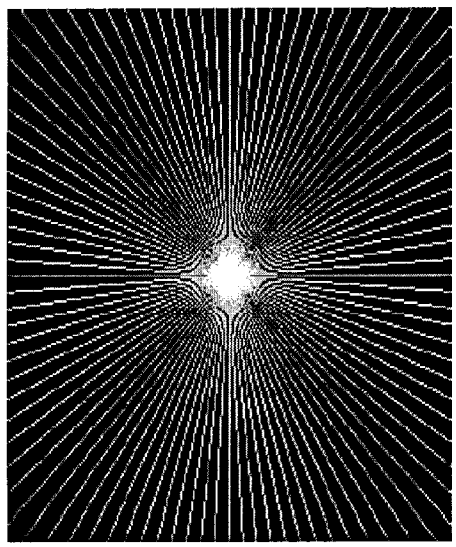
FIG. 10 is a further illustrative example of comparison of images including an image generated using FBP and a reconstructed image generated according to compressed sensing image reconstruction according to some embodiments.
Figure 10:
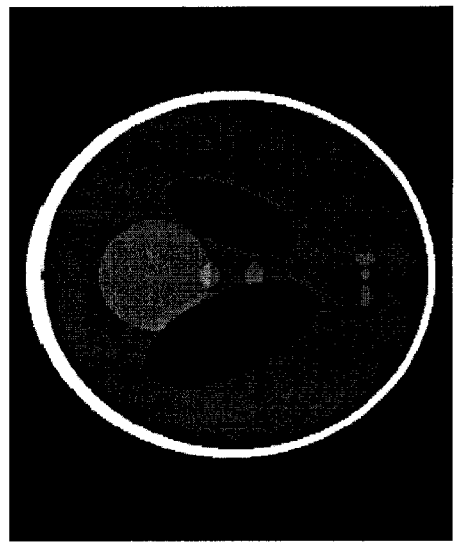
Figure 10:
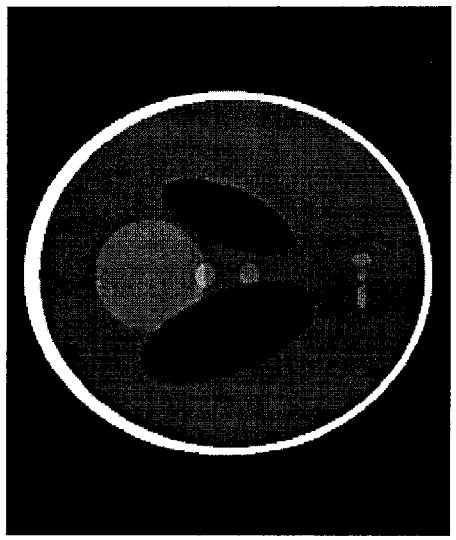
Figure 10:
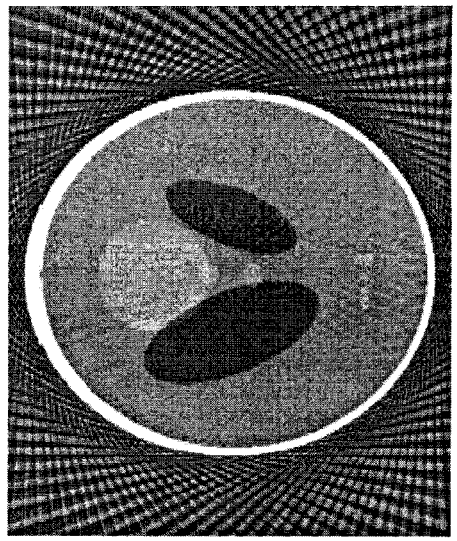

FIG. 9 gives an example indication of the performance of CS when entire swaths of scan data are unavailable, such as when a complete rotation cannot be obtained due to a patient's quickly-beating heart. In cases where there is no scan time limitation but it is still desirable to reduce the patient's radiation dose, one can safely undersample the specimen even further (and with reduced noise artifacts) by taking a more uniform sampling. FIG. 10 compares an example of the embodiments described herein using CS methodology to FBP and FBP-based methods where exposure angles are uniformly undersampled. Alternative reasons to deliberately undersample may also include cases where super-resolution images of the specimen are desired, among others.

FIG. 10 shows an example of CS performance with uniform undersampling. Top left: Original 512×512 image (image 430), which can be reconstructed by FBP from a complete set of 1200 projections and 180 views. Top right: 50 views may be sufficient for a CS reconstruction (image 432). Bottom left: image reconstructed from 50 views and FBP, $$\text{error} = \frac{\|f - \tilde{f}_{FBP}\|^2}{\|f\|^2} \times 100\% = 0.14\% \text{ (image 428).}$$

Bottom right: image reconstructed from 50 views with an example of the embodiments described herein using the CS method, $$\text{error} = \frac{\|f - \tilde{f}_{CS}\|^2}{\|f\|^2} \times 100\% = 0.14\%. \text{ (image 434)}$$

Figure 11:
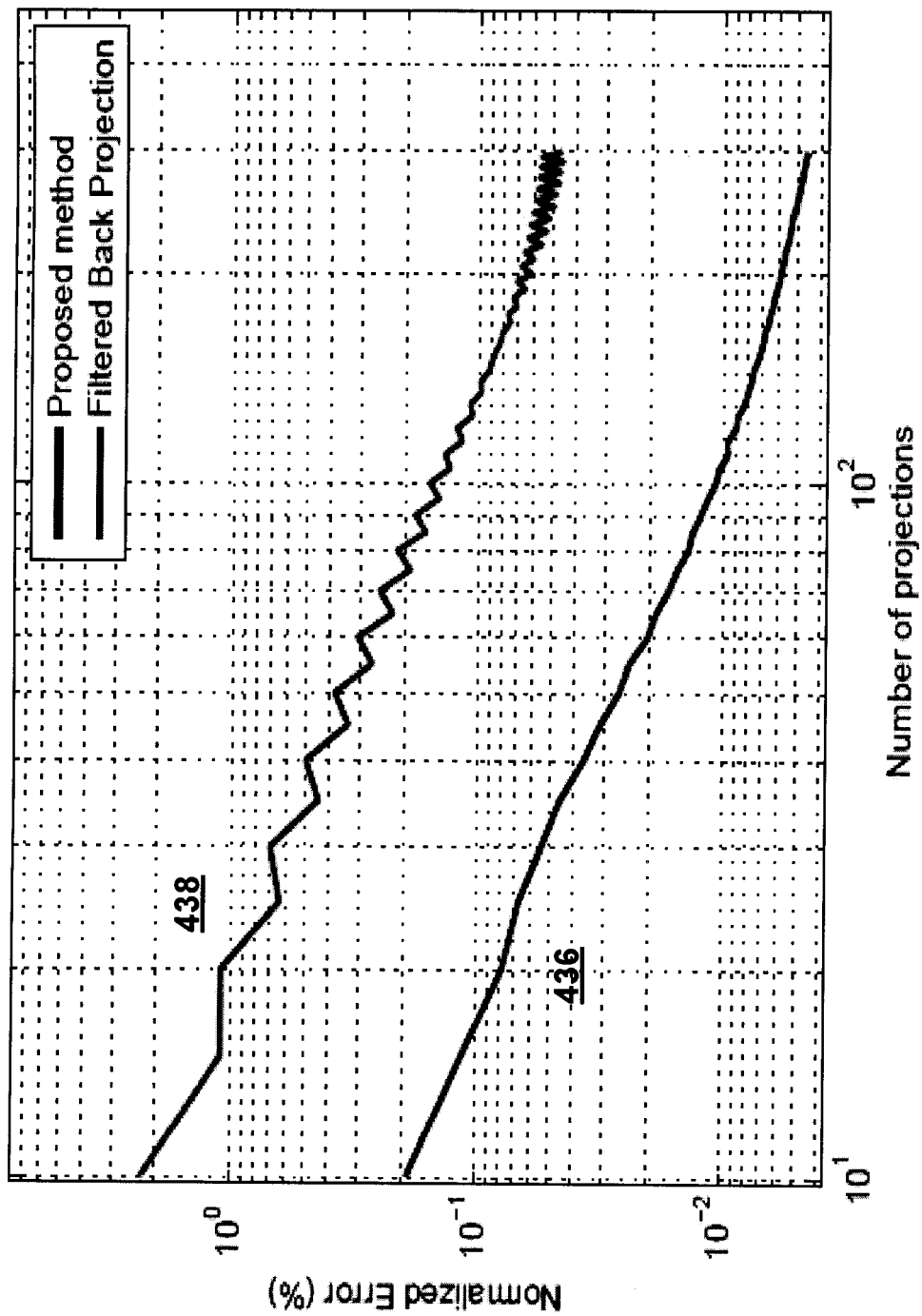
FIG. 11 is an example chart illustrative of an error reduction trend of image reconstruction according to embodiments described herein as compared to FBP.

FIG. 11 illustrates reduction in $$\text{error} = \left(\frac{\|f - \tilde{f}\|^2}{\|f\|^2}\%\right)$$

of FBP and CS with increasing numbers of equi-angle spaced projections. The X-ray tube current in this scan was 50 mAs with 120 kV.

As seen in FIG. 10, an example of the disclosed CS method was found to outperform FBP using only 50 projections. FIG. 11 shows the error reduction trend with increasing dose comparing the proposed embodiments (line 436) to FBD (line 438). In CT imaging, the dose reduction engendered by this intentional undersampling may be over 72% given the reduced number of exposures necessary for reconstructing an acceptable image; in MRI or other tomography techniques, scan times or cost may be similarly reduced. As seen in FIG. 12, similar benefits can be seen in more complicated specimens.

In FIG. 12, image size is 512×512. Top left: Original 512×512 image (image 442), which can be reconstructed by FBP from a complete set of 1200 projections and 180 views. Top right: 100 views was found to be sufficient for a CS reconstruction (image 444). Bottom left: image reconstructed from 100 views and FBP, $$\text{error} = \frac{\|f - \tilde{f}_{FBP}\|^2}{\|f\|^2} \times 100\% = 16\% \text{ (image 440).}$$

Bottom right: image reconstructed from 100 views with an example of the disclosed CS method, $$\text{error} = \frac{\|f - \tilde{f}_{CS}\|^2}{\|f\|^2} \times 100\% = 1.0\% \text{ (image 446)}$$

Noise and Confidence

In the previous section it was discussed that CS solutions to tomography problems (such as CT imaging) can be obtained by solving (7). By default, CS weighs all observational evidence equally. However, in the case of CT, different exposures (e.g., with distinct photon counts) may have different levels of Poisson noise and in general for all tomographic techniques, noise may not be uniform across measurements. Moreover, when interpolation is required (such as with some parallel, fan beam, C-arm, conical and helical CT, or some reconstruction protocols with any type of structured or random MRI undersampling), interpolated Fourier coefficients closer to observed coefficients tend to have smaller interpolation artifacts. In some examples of the present disclosure, a modification to CS may be used that allows confidence in a particular measurement to influence the weight it is given in the reconstruction.

In some examples, the model-signal divergence penalty (the first term of (7)) may be made to coincide with the log likelihood of the observed signal under the postulated model x, yielding a Bayesian-optimal reconstructed or recovered image or measurement. Consider a noise result directly applicable to CT imaging: Poisson noise levels due to limited photon count.

Beer's Law Compensation

Below are described the mathematics used to account for the exponential decay of ray intensity as it propagates through a constant medium. Suppose a particular ray r passes through the specimen from $x_0$ to $x_1$, the start and end points of the ray. The mass along this ray the total mass $m_r$ is given by $$m_r = \int_{x_0}^{x_1} \rho(x) dx \qquad (8)$$

By Beer's law, the observed signal $S_r$ (the expected photon count) is given by $$S_r = S_0 e^{-\beta m_r} \qquad (9)$$

where $S_0$ is the expected count with an empty specimen and $\beta$ is the Beer's Law exponential decay constant. A transform of $S_r$ may be found such that $m_r$ is linear, allowing the use linear reconstruction techniques without introducing artifacts. Taking the natural log of (9), $$\ln(S_r) = \ln(S_0) - \beta m_r \qquad (10)$$

$$m_r = \frac{\ln\left(\frac{S_0}{S_r}\right)}{\beta}$$

Transforming from raw count to expected mass using (10) may compensate for exponential losses.

Accounting for Poisson, Fixed and Interpolation Noise

In another example, herein is described a noise-weighted variant of CS (or alternative) that maps the logarithm of signal likelihood to the penalty term for the divergence of y and Ax by introducing a confidence vector c. For the example TV enhanced BPDN described above, the modification may be as follows:

$$\operatorname*{argmin}_{x} \frac{1}{2}\|(c \cdot y) - (c \cdot ax)\|_2^2 + \lambda_1 \|x\|_1 + \lambda_2 TV(f) \qquad (11)$$

where · is element-by-element multiplication. If c is proportional to the reciprocal of the standard deviation of the noise (or more generally, the uncertainty in the measurements), and the noise is Gaussian, (11) yields a maximum a posteriori (MAP) model of the data, as log likelihood scales with $\|(c \cdot y) - (c \cdot ax)\|_2^2$.

The c factor here has been used with a specific BPDN formulation, but this example may include the process of scaling signal dimensions by any scalar, static nonlinearity of multivariate transformation such that the term of the optimization problem penalizing divergence between y and Ax becomes closer to being monotonically related to the likelihood of x given y and appropriate noise and artifact considerations (including but not limited to interpolation artifacts).

In the case of CT imaging with the central slice theorem, the noise associated with a particular measurement $S_r$ may be defined to have three substantial components: a signal-independent part n from the device, a Poisson term $\sqrt{S_r}$ and an interpolation uncertainty term $u_r$. The noise-aware correction to relationship between $S_r$ and $m_r$ of (9) may be therefore:

$$S_r = S_0 e^{-\beta m_r \pm n \pm u_r} \pm \sqrt{S^x} \quad (12)$$

Adding the noises in quadrature and invoking a Gaussian noise assumption, the expected total noise has standard deviation proportional to $\sqrt{n^2 + u_r^2 + S_r}$. The variation in $m_r$ expected under this noise may be determined by passing it through the transformations of (10). Consider a mass $m_r^l$ (superscript l indicates the lower limit of photon count) one noise standard deviation above the expected value for $m_r$.

$$S_r^l - \sqrt{n^2 + u_r^2 + S_r^l} = S_0 e^{-\beta m_r^l} \quad (13)$$

$$\ln\left(S_r^l - \sqrt{n^2 + u_r^2 + S_r^l}\right) = \ln(S_0) - \beta m_r^l$$

$$m_r^l = \frac{\ln\left(\frac{S_0}{S_r^l - \sqrt{n^2 + u_r^2 + S_r^l}}\right)}{\beta}$$

Subtracting (10) from (13) gives the expected noise in $m_r$:

$$\delta m_r = \frac{1}{\beta}\left[\ln\left(\frac{S_0}{S_r - \sqrt{n^2 + u_r^2 + S_r}}\right) - \ln\left(\frac{S_0}{S_r}\right)\right] \quad (14)$$

$$= \frac{1}{\beta}\left[\ln\left(\frac{S_r}{S_r - \sqrt{n^2 + u_r^2 + S_r}}\right)\right]$$

$$= \frac{1}{\beta}\left[-\ln\left(1 - \frac{\sqrt{n^2 + u_r^2 + S_r}}{S_r}\right)\right]$$

The value of $\delta m_r$ may be somewhat approximate, in that it assumes Gaussian noise whereas Poisson noise is not truly Gaussian, and in that it uses one point in the distribution to estimate total noise. From (14), the following c factor may allow the modified BPDN solution to coincide with the Bayesian MAP estimate given priors:

$$c \propto \frac{-\beta}{\ln\left(1 - \frac{\sqrt{n^2 + u_r^2 + S_r}}{S_r}\right)} \quad (15)$$

The appropriate application of c may result in clearer images. As seen in FIG. 13, SNR can be improved using correct information regarding variable noise levels in the raw data. A principled consideration of noise (e.g. using (11) rather than (7)) combined with correct prior expectations about the structure of the specimen may thus yield a better image than FBP, which is currently the most common reconstruction method used in CT scans.

FIG. 13 shows example comparisons of the good, bad, and flat confidence coefficients. Top left shows the image reconstructed using FBP from 50 noisy projections, error is 43% (image 450). Top right shows the image reconstructed under (15) and (11) with a c based on actual noise, error is 0.12% (image 452), Bottom left shows the reconstruction under (15) and (11) with entries in c swapped in order from what would be appropriate, error is 9% (448). Bottom right shows the image using BPDN without variable confidence (7), error is 2% (image 454).

In general, the inclusion of a c term may be possible in CT scans by constructing the image from the raw sensor outputs, and not from an intermediate form such as the FBP estimate of the image given partial, full, or overcomplete data. However, in some examples the presently disclosed methods and systems may include the possibility of using a c term in conjunction with an intermediate image representation when differential noise information is known about this intermediate representation as well.

Embodiments described herein, in some examples, provides tomography methods which leverage the central slice theorem to compute images or measurements faster than current methods. One example implementation described herein uses CS. CS may make it possible to recover images with more pixels than the total number of observations, while also denoising the image. Embodiments described herein may apply to any tomographic scanning technique where the central slice theorem may be used to speed synthesis of results based on data and prior expectations about the specimen, noise and artifacts, including CT, MRI and other methodologies, in undercomplete, complete and overcomplete data collection regimes.

In some examples, embodiments described herein provide methods and systems that may be able to accelerate the process of solving CT imaging compressed sensing problems. Embodiments described herein may help allow the use of full compressed sensing in the realm of clinically-useful techniques: in some examples, it has been found that benchmarked CT-scale full CS may be carried out in mere seconds on modest computer hardware, using examples of the disclosed methods and systems.

In some examples, embodiments described herein may provide clinical benefit in (for instance) radiation-intense CT scans. CT scans that benefit from CS have been sought for years. In fact, CS reconstructions based on the FBP solution are just now becoming popular. However, current CT computations of full CS typically are so computationally expensive that they are not clinically useful. The present disclosure may provide a CS framework that may hold advantages over FBP-based CS solutions including one or more of, for example: greater speed, useful with incomplete scan data, and ability to account for variable levels of noise from different observations.

In some examples, embodiments described herein may allow for decrease in the computational cost of computing full CS (or alternatives to CS) reconstructions, which may make it possible to reconstruct CT, MRI or other images or measurements relatively quickly—for CT scans, computation time in some examples has been found to be comparable with FBP for standard-sized images.

In some examples, embodiments described herein may be applied to existing or future scanning hardware and modest computational equipment may result in substantial clinical improvements, including CT scans that may be simultaneously more diagnostically powerful and deliver a lower radiation dose.

FIG. 14 is an example chart comparing computation time for an Art-Total variation minimization based method which use matrix multiplication (such as PICCS for example, as shown by line 456) and the compressed sensing image reconstruction according to some embodiments (as shown by line 458). Image size is 256×256 in this example. In PICCS the computation speed decreases by increasing the number of projections since the matrix A which models the projections gets larger, while increasing the number of projection increases the image quality. Thus, there is a computation time vs. image quality trade off. However, embodiments described herein may be almost independent of the projection number and is much faster. In addition, a computer with 8 GB of RAM could not handle images larger than 256×256 while the proposed method can easily handle larger images such as 512×512 as shown in the other figures. The beams are interpolated on pseudo-polar grids in this example which is between polar and Cartesian and helps to reduce the reconstruction error while by using fast pseudo-polar transform algorithms still the computations time is much smaller than conventional CS-based recovery algorithms.

FIG. 15 is another illustrative example of comparison of images with different confidence matrices according to some embodiments. Left image (image 460) is recovered with bad confidence matrix, and right image (image 462) is the same image recovered by a good confidence matrix. A bad confidence matrix may be a matrix which is filled with random values between 0 and 1 and good confidence may be the matrix shown in FIG. 16, which shows the distance between the exact measured data and the interpolated data.

FIG. 16 is an illustrative example of a confidence matrix 464. The example confidence matrix 464 illustrates whiter pixels as showing higher confidence and darker pixels as showing the lower confidence. Black regions are the parts from which we have no information. This confidence matrix may be a mixture of the additional noise to the system as is described by equation (15) and interpolation error. The interpolation error may be represented by the distance between the closest measured data to the interpolated data and the interpolated data. The closer the measured data is to the interpolated data, which means the error is lower, the confidence coefficient is higher.

Embodiments described herein are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

The invention claimed is:

1. A method for image reconstruction, the method comprising:
   receiving, at a computing device comprising a processor and a data storage device, signals representing a set of raw image data;
   performing, using the processor, a 1-dimensional Fourier transform on the set of raw image data to convert the set of raw image data into a partial Fourier domain;
   determining an interpolation of the set of raw image data in the partial Fourier domain from a polar coordinate system to a pseudo-polar or Cartesian coordinate system;
   determining, using the processor, a set of reconstructed image data from the set of raw image data in the partial Fourier domain, based on an optimization model having a confidence matrix to compromise noise of sensors used to generate the set of raw image data;
   performing, using the processor, an inverse operation on the set of reconstructed image data to convert the set of reconstructed or recovered image data into an image domain; and
   generating signals representing the set of reconstructed image data.

2. The method of claim 1, wherein the set of raw image data is in a projection domain or a raw data domain.

3. The method of claim 1, further comprising using the signals representing the set of reconstructed or recovered image data to generate a reconstructed image on a display.

4. The method of claim 1, wherein the optimization model is based on a set of basis data in a domain selected from the group consisting of a Wavelet domain, Curvelet domain, or other sparsifying transform domain.

5. The method of claim 1, wherein the optimization model is based on a set of selected regularization parameters.

6. The method of 1, wherein the set of raw image data is based on parallel beam geometrics.

7. The method of claim 1, wherein the optimization model comprises a confidence matrix to control interpolation error caused by the conversion from the polar coordinate system to the pseudo-polar or Cartesian coordinate system.

8. The method of claim 1, further comprising applying a weighting to each data point in the pseudo-polar or Cartesian coordinate system, based on a known amount of confidence in interpolation between the polar coordinate system and the pseudo-polar or the Cartesian coordinate system.

9. The method of claim 8, wherein the method further comprises using a confidence matrix to control error caused by the rebinning.

10. The method of claim 1, wherein the set of raw image data is based on non-parallel beam geometries, and wherein the method further comprises rebinning the set of raw image data based on parallel beam geometries.

11. The method of claim 10, wherein the set of raw image data is based on non-parallel beam geometries comprises fan beam and cone beam geometries.

12. The method of claim 1, wherein the set of raw image data may be acquired using computed tomography (CT) imaging, parallel beam CT scanning, cone beam CT scanning, C-arm scanning, helical CT, scanning magnetic resonance imaging (MRI), electron tomography or other imaging modality.

13. The method of claim 1, wherein the set of raw image data comprises image data selected from the group consisting of a set of incomplete raw image data, a set of complete raw image data, and a set of overcomplete raw image data.

14. The method of claim 1, wherein the optimization model comprises modified compressed sensing solvers.

15. The method of claim 1, wherein the set of raw image data is generated by dual energy X-ray computed tomography (CT) and comprises two partial sets of image data gathered with different energies to reduce the exposed X-ray dose.

16. A system for image reconstruction, the system comprising a processor coupled to a memory having computer-readable instructions recorded thereon, the computer-readable instructions, when executed, may cause the system to configure:
   an image data acquisition unit for receiving signals representing a set of raw image data;
   a transform unit for performing a 1-dimensional Fourier transform on the set of raw image data to convert the set of raw image data into a partial Fourier domain and determine an interpolation of the set of raw image data from a polar coordinate system to a pseudo-polar or Cartesian coordinate system;
   an optimization unit for determining a set of reconstructed image data from the set of raw image data in the partial Fourier domain, based on an optimization model having a confidence matrix to compromise noise of sensors used to generate the set of raw image data; and an inverse unit for performing an inverse operation on the set of reconstructed or recovered image data to convert the set of reconstructed image data into an image domain;

wherein the processor is further configured for generating signals representing the set of reconstructed image data.

17. The system of claim 16, further comprising an interpolation module for determining an interpolation of the set of raw image data in the Fourier domain from a polar coordinate system to a pseudo-polar or Cartesian coordinate system.

18. The system of claim 16, wherein the set of raw image data is based on non-parallel beam geometries, and wherein the system further comprises a rebinning module for rebinning the set of raw image data based on parallel beam geometries.

* * * * *